US008744591B2

(12) United States Patent
Davis et al.

(10) Patent No.: US 8,744,591 B2
(45) Date of Patent: Jun. 3, 2014

(54) STORING IMAGE OF THERAPY REGION IN IMPLANTABLE MEDICAL DEVICE

(75) Inventors: Jon P. Davis, St. Michael, MN (US); Steven M. Goetz, North Oaks, MN (US); Nathan A. Torgerson, Andover, MN (US); Wende L. Dewing, Edina, MN (US); Ashish Singal, Blaine, MN (US); Lynn A. Davenport, Roseville, MN (US); Rajeev M. Sahasrabudhe, Maple Grove, MN (US); Brent A. Huhta, Big Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 778 days.

(21) Appl. No.: 12/771,652

(22) Filed: Apr. 30, 2010

(65) Prior Publication Data

US 2011/0093047 A1    Apr. 21, 2011

Related U.S. Application Data

(60) Provisional application No. 61/253,756, filed on Oct. 21, 2009, provisional application No. 61/260,707, filed on Nov. 12, 2009, provisional application No. 61/253,766, filed on Oct. 21, 2009, provisional application No. 61/260,712, filed on Nov. 12, 2009, provisional application No. 61/253,759, filed on Oct. 21, 2009, provisional application No. 61/260,644, filed on Nov. 12, 2009.

(51) Int. Cl.
    *A61N 1/08*    (2006.01)
(52) U.S. Cl.
    USPC .............................................. 607/60; 607/32
(58) Field of Classification Search
    USPC .......................................................... 607/60
    See application file for complete search history.

(56) References Cited

U.S. PATENT DOCUMENTS

| 3,069,654 A | 12/1962 | Hough |
| 5,241,472 A | 8/1993 | Gur et al. |

(Continued)

FOREIGN PATENT DOCUMENTS

| AU | 709374 | 12/1997 |
| WO | 97/43871 | 11/1997 |

(Continued)

OTHER PUBLICATIONS

Notification of Transmittal of the International Search Report and the Written Opinion of the International Searching Authority for Corresponding Patent Application No. PCT/US10/52621, Mailed Mar. 2, 2011, 11 pages.

(Continued)

*Primary Examiner* — Michael Kahelin
(74) *Attorney, Agent, or Firm* — Shumaker & Sieffert, P.A.

(57) ABSTRACT

This disclosure describes techniques for obtaining an image of an anatomical implant region where leads associated with an implantable medical device are implanted in a patient, manipulating the image to show lead locations and placements, performing necessary image compression and manipulations, adjusting the image to associate it with information (e.g., patient, metadata, annotations, etc.) useful to a subsequent programmer retrieving the image, and transferring a copy of the captured image to the implantable medical device. The image stored in the implantable medical device may be retrieved at a later time by a user of programmer, where the user can use the image and other associated information to program subsequent therapy.

56 Claims, 7 Drawing Sheets

(56) References Cited

U.S. PATENT DOCUMENTS

| | | | |
|---|---|---|---|
| 5,722,999 A * | 3/1998 | Snell | 607/32 |
| 6,026,142 A | 2/2000 | Gueziec et al. | |
| 6,358,245 B1 | 3/2002 | Edwards et al. | |
| 6,373,918 B1 | 4/2002 | Wiemker et al. | |
| 6,393,325 B1 | 5/2002 | Mann et al. | |
| 6,625,482 B1 | 9/2003 | Panescu et al. | |
| 6,697,664 B2 | 2/2004 | Kienzle, III et al. | |
| 6,993,384 B2 | 1/2006 | Bradley et al. | |
| 7,044,942 B2 | 5/2006 | Jolly et al. | |
| 7,239,920 B1 | 7/2007 | Thacker et al. | |
| 7,346,382 B2 | 3/2008 | McIntyre et al. | |
| 7,477,723 B2 | 1/2009 | Kamegawa et al. | |
| 7,505,809 B2 | 3/2009 | Strommer et al. | |
| 7,567,834 B2 | 7/2009 | Clayton et al. | |
| 7,623,918 B2 | 11/2009 | Goetz | |
| 2003/0013977 A1 | 1/2003 | Daum | |
| 2003/0139781 A1 | 7/2003 | Bradley et al. | |
| 2004/0088027 A1 | 5/2004 | Burnes et al. | |
| 2004/0098063 A1 | 5/2004 | Goetz | |
| 2004/0210273 A1 | 10/2004 | Wang | |
| 2004/0215239 A1 | 10/2004 | Favet et al. | |
| 2005/0131474 A1 | 6/2005 | Jenkins et al. | |
| 2005/0171587 A1 | 8/2005 | Daglow et al. | |
| 2006/0122653 A1 | 6/2006 | Bradley et al. | |
| 2006/0122654 A1 | 6/2006 | Bradley et al. | |
| 2007/0106360 A1 | 5/2007 | Gibson et al. | |
| 2007/0142888 A1 | 6/2007 | Chavez | |
| 2007/0185544 A1 | 8/2007 | Dawant et al. | |
| 2007/0203539 A1 | 8/2007 | Stone et al. | |
| 2007/0203545 A1 | 8/2007 | Stone et al. | |
| 2007/0203546 A1 | 8/2007 | Stone et al. | |
| 2007/0255339 A1 | 11/2007 | Torgerson | |
| 2007/0288064 A1 | 12/2007 | Butson et al. | |
| 2007/0288070 A1 | 12/2007 | Libbus et al. | |
| 2008/0154340 A1 | 6/2008 | Goetz et al. | |
| 2008/0218510 A1 | 9/2008 | Grass et al. | |
| 2008/0288029 A1 | 11/2008 | Healy et al. | |
| 2009/0012416 A1 | 1/2009 | Belalcazar et al. | |
| 2009/0083070 A1 | 3/2009 | Giftakis et al. | |
| 2009/0118635 A1 | 5/2009 | Lujan et al. | |
| 2009/0196471 A1 | 8/2009 | Goetz et al. | |
| 2009/0196472 A1 | 8/2009 | Goetz et al. | |
| 2009/0198306 A1 | 8/2009 | Goetz et al. | |
| 2010/0135553 A1 | 6/2010 | Joglekar | |
| 2011/0313487 A1 | 12/2011 | Kokones et al. | |

FOREIGN PATENT DOCUMENTS

| | | |
|---|---|---|
| WO | 99/37358 | 7/1999 |
| WO | 01/54579 | 2/2001 |
| WO | 2007/007058 | 1/2007 |
| WO | 2010030904 A2 | 3/2010 |

OTHER PUBLICATIONS

Office Action for U.S. Appl. No. 12/771,763, dated Sep. 15, 2011, 14 pages.

Response to Office Action for U.S. Appl. No. 12/771,763, filed Dec. 14, 2011, 13 pages.

Written Opinion of international application No. PCT/US2010/052621, mailed Jan. 20, 2012, 7 pages.

Reply to Written Opinion dated Jan. 20, 2012 for corresponding patent application No. PCT/US2010/052621, filed Feb. 20, 2012, 13 pages.

Notification of Transmittal of the International Preliminary Report on Patentability for corresponding patent application No. PCT/US2010/052621, dated Mar. 7, 2012, 18 pages.

McIntyre et al., "Electric Field and Stimulating Influence Generated by Deep Brain Stimulation of the Subthalamic Nucleus," Clinical Neurophysiology, vol. 115, 2004, pp. 589-595.

Freeman et al. "Determining the Minimum-Area Encasing Rectangle for an Arbitrary Closed Curve," Comm. ACM, Jul. 1975, pp. 409-413.

Lindeberg, "Feature Detection With Automatic Scale Selection," International Journal of Computer Vision 30 (2), 1998, pp. 79-116.

Lowe, "Distinctive Image Features from Scale-Invariant Keypoints," International Journal of Computer Vision 60 (2), 2004, pp. 91-110.

Lindeberg, "Detecting Salient Blob-Like Image Structures and Their Scales with a Scale-Space Primal Sketch: A Method for Focus-of-Attention," International Journal of Computer Vision 11 (3), 1993, pp. 283-318.

U.S. Appl. No. 12/906,418, by Steven M. Goetz, filed Oct. 18, 2010.

U.S. Appl. No. 12/771,763, by Jon P. Davis, filed Apr. 30, 2010.

Notification of Transmittal of the International Search Report and the Written Opinion of the International Searching Authority for corresponding patent application No. PCT/US2010/052573, mailed Feb. 9, 2011, 10 pages.

Final office action for U.S. Appl. No. 12/771,763, mailed Feb. 16, 2012, 10 pages.

Reply to Written Opinion for corresponding patent application No. PCT/US2010/052621, filed Aug. 18, 2011, 11 pages.

Response to office action dated May 16, 2012 for U.S. Appl. No. 12/771,763, 15 pages.

Response to Office Action for U.S. Appl. No. 12/771,763, filed Jun. 18, 2013, 25 pages.

Office Action for U.S. Appl. No. 12/771,763, mailed Mar. 18, 2013, 18 pages.

Response to Office Action dated Aug. 20, 2013, from U.S. Appl. No. 12/771,763, filed Oct. 21, 2013, 6 pp.

Office action for U.S. Appl. No. 12/771,763, mailed Aug. 20, 2013, 18 pages.

* cited by examiner

STORING IMAGE OF THERAPY REGION IN IMPLANTABLE MEDICAL DEVICE

This application claims the benefit of U.S. Provisional Application No. 61/253,756, entitled "STORING IMAGE OF THERAPY REGION IN IMPLANTABLE MEDICAL DEVICE," filed on Oct. 21, 2009; U.S. Provisional Application No. 61/260,707, entitled "STORING IMAGE OF THERAPY REGION IN IMPLANTABLE MEDICAL DEVICE," filed on Nov. 12, 2009; U.S. Provisional Application No. 61/253,766, entitled "ASSIGNMENT AND MANIPULATION OF IMPLANTABLE LEADS IN DIFFERENT ANATOMICAL REGIONS WITH IMAGE BACKGROUND," filed on Oct. 21, 2009; U.S. Provisional Application No. 61/260,712, entitled "ASSIGNMENT AND MANIPULATION OF IMPLANTABLE LEADS IN DIFFERENT ANATOMICAL REGIONS WITH IMAGE BACKGROUND," filed on Nov. 12, 2009; U.S. Provisional Application No. 61/253,759, entitled, "MANAGING ELECTRICAL STIMULATION THERAPY BASED ON VARIABLE ELECTRODE COMBINATIONS," filed on Oct. 21, 2009; and U.S. Provisional Application No. 61/260,644, entitled, "MANAGING ELECTRICAL STIMULATION THERAPY BASED ON VARIABLE ELECTRODE COMBINATIONS," filed on Nov. 12, 2009, the entire contents of each being incorporated herein by reference.

TECHNICAL FIELD

The disclosure relates to medical devices and, more particularly, to medical devices that deliver electrical stimulation therapy.

BACKGROUND

Medical devices may be used to treat a variety of medical conditions. Medical electrical stimulation devices, for example, may deliver electrical stimulation therapy to a patient via implanted electrodes. Electrical stimulation therapy may include stimulation of nerve, muscle, or brain tissue, or other tissue within a patient. An electrical stimulation device may be fully implanted within the patient. For example, an electrical stimulation device may include an implantable electrical stimulation generator and one or more implantable leads carrying electrodes. Alternatively, the electrical stimulation device may comprise a leadless stimulator. In some cases, implantable electrodes may be coupled to an external electrical stimulation generator via one or more percutaneous leads or fully implanted leads.

Medical electrical stimulators may be used to deliver electrical stimulation therapy to patients to relieve a variety of symptoms or conditions such as chronic pain, tremor, Parkinson's disease, depression, epilepsy, urinary or fecal incontinence, pelvic pain, sexual dysfunction, obesity, or gastroparesis. An electrical stimulator may be configured to deliver electrical stimulation therapy via leads that include electrodes implantable proximate to the spinal cord, pelvic nerves, gastrointestinal organs, peripheral nerves, or within the brain of a patient. Stimulation proximate the spinal cord and within the brain are often referred to as spinal cord stimulation (SCS) and deep brain stimulation (DBS), respectively.

A clinician selects values for a number of programmable stimulation parameters in order to define the electrical stimulation therapy to be delivered to a patient. For example, the clinician may select a current or voltage amplitude of the stimulation, and various characteristics of the stimulation waveform. In addition, the clinician may specify an electrode configuration used to deliver stimulation, including selected electrode combinations and electrode polarities. If the stimulation is delivered in the form of pulses, for example, the clinician may specify a pulse width and pulse rate. A set of parameter values may be referred to as a stimulation program. A program group may include multiple programs. Multiple programs in a program group may be delivered on a simultaneous, time-interleaved, or overlapping basis.

SUMMARY

Generally, this disclosure describes techniques for storage of images of implant regions in an implantable medical device. The implant regions may be anatomical implantation regions where elements associated with the implantable medical device may be implanted, such as, for example, lumbar spine, epidural thoracic, etc. The images may convey information about therapies delivered by the medical devices, and anatomical implantation regions within the patients to whom the therapies are delivered. In some examples, the image may be obtained by an external programmer for the implantable medical device. The external programmer may obtain the image by capturing an image of a hard copy or electronic display that presents the image. In other examples, the external programmer may obtain the image directly from a device that forms the image or from an intermediate device that stores, processes, or forwards the images. In other examples, the external programmer may obtain the image from an imaging system or device by transferring the image using telemetry, by copying the image using digital media, or by a physical connection between the imaging system/device and the external programmer. In each case, the image may be obtained by the programmer and transferred to the implantable medical device, e.g., for later retrieval and viewing by a clinician, patient, or other user. The image of an implant region may be stored and/or presented in conjunction with medical leads implanted in the region.

In one example, the disclosure is directed to a device for communication with an implantable electrical stimulator, the programmer comprising an image acquisition device that obtains at least one image of at least one anatomical region of a patient and at least one medical lead implanted within the at least one anatomical region, wherein the at least one lead is associated with the implantable medical device, and a telemetry device that transmits the at least one image to the implantable medical device for storage in the implantable medical device.

In another example, the disclosure is directed to a method comprising obtaining by a device at least one image of at least one anatomical region of a patient and at least one medical lead implanted within the at least one anatomical region, wherein the at least one lead is associated with an implantable medical device, and transmitting the at least one image to the implantable medical device for storage in a storage device in the implantable medical device.

In another example, the disclosure is directed to a device comprising means for obtaining at least one image of at least one anatomical region of a patient and at least one medical lead implanted within the at least one anatomical region, wherein the at least one lead is associated with an implantable medical device, and means for transmitting the at least one image to the implantable medical device for storage in a storage device in the implantable medical device.

In another example, the disclosure is directed to a computer-readable medium comprising instructions that, upon execution, cause a processor to obtain at least one image of at least one anatomical region of a patient and at least one medical lead implanted within the at least one anatomical region, wherein the at least one lead is associated with the implantable medical device, and transmit the at least one image to the implantable medical device for storage in a storage device in the implantable medical device.

In another example, the disclosure is directed to a an implantable medical device comprising a therapy delivery module, a processor that controls the therapy delivery module to deliver therapy, a telemetry module that receives, from an external device via telemetry, at least one image of at least one anatomical region of a patient and at least one lead implanted within the at least one anatomical region, wherein the at least one lead is associated with the implantable medical device, and a memory that stores the image.

The details of one or more aspects of the disclosure are set forth in the accompanying drawings and the description below. Other features, objects, and advantages will be apparent from the description and drawings, and from the claims.

DETAILED DESCRIPTION

The examples of this disclosure provide a user with the ability to capture and store a copy of an image of an anatomical implant region of a patient, in the patient's implantable medical device (IMD). The techniques of this disclosure describe how to capture an image, then manipulate it before storing it in an IMD. Manipulating an image may involve, for example, resizing, cropping, zooming, panning, and annotating the image. The image may show, for example, placement of leads through which the IMD delivers therapy to the patient. Information related to the patient and the therapy may be also programmed into the image as metadata. The image may be stored in the IMD and may be retrieved at a later time by a programmer to utilize in the application and programming of future therapy associated with the implant region associated with the image.

Figure 1:
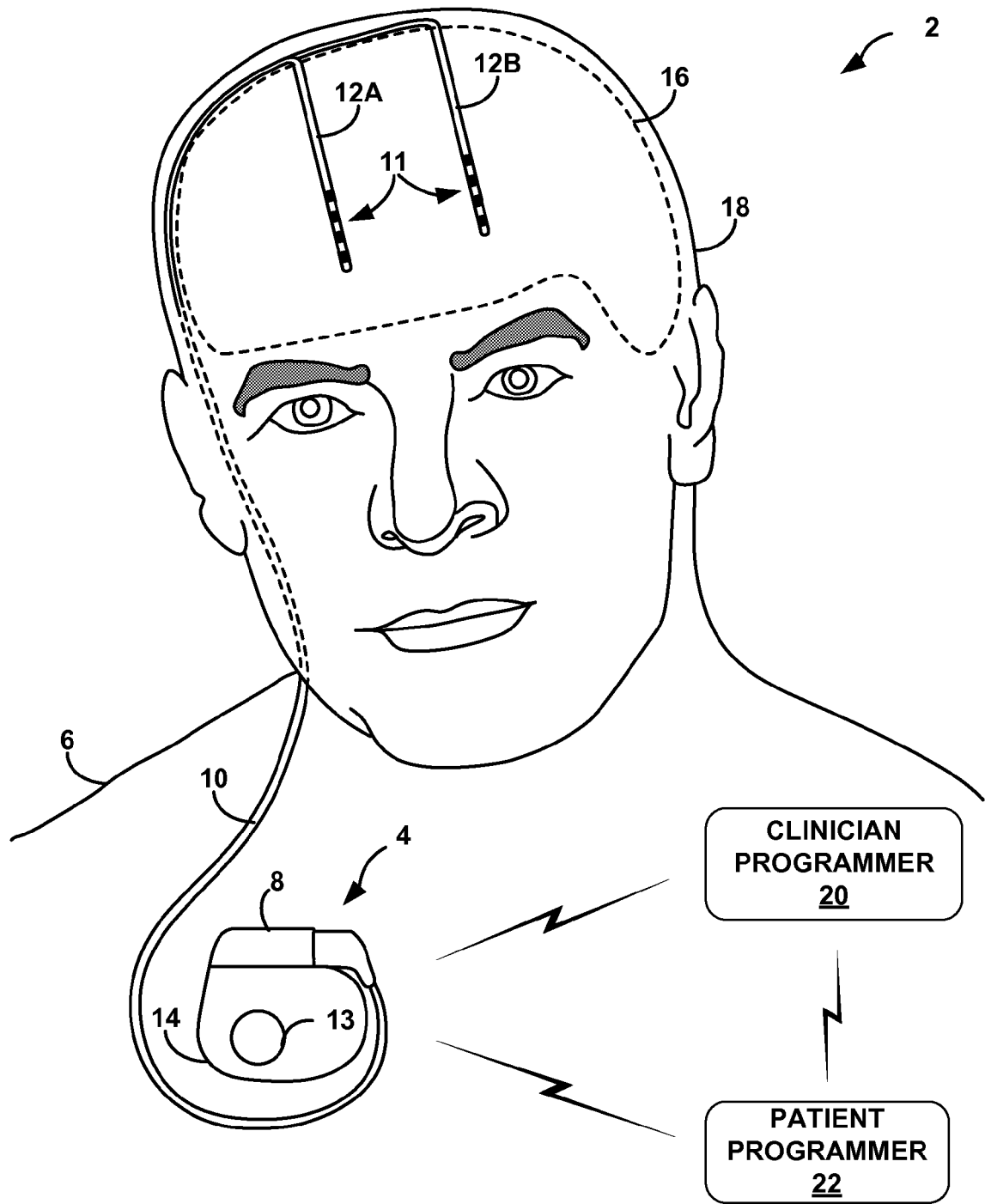
FIG. 1 is a conceptual diagram illustrating an example therapy system that includes an implantable stimulator coupled to a stimulation lead.

FIG. 1 is a conceptual diagram illustrating an example therapy system 2 including an implantable electrical stimulator 4 that may be used to deliver stimulation therapy to patient 6. Patient 6 ordinarily, but not necessarily, will be a human. Generally, therapy system 2 includes implantable electrical stimulator 4 that delivers electrical stimulation to patient 6 via one or more implantable electrodes 11. The implantable electrodes 11 may be deployed on one or more implantable medical leads, such as implantable medical lead 10, and in some cases on a can electrode. The electrical stimulation may be in the form of controlled current or voltage pulses or substantially continuous waveforms. Various parameters of the pulses or waveforms may be defined by one or more stimulation programs. The pulses or waveforms may be delivered substantially continuously or in bursts, segments, or patterns, and may be delivered alone or in combination with pulses or waveforms defined by one or more other stimulation programs. Although FIG. 1 shows a fully implantable stimulator 4, techniques described in this disclosure may be applied to external stimulators having electrodes deployed via percutaneously implantable leads with a patch electrode or other indifferent electrode attached externally to serve as the can or case. One or more of the electrodes may be located on a housing 14, i.e., "can" or "case," of the implantable stimulator 4. In addition, in some cases, implantable electrodes may be deployed on a leadless stimulator.

In the example illustrated in FIG. 1, implantable stimulator 4 is implanted within a subcutaneous pocket in a clavicle region of patient 6. Stimulator 4 generates programmable electrical stimulation, e.g., a current waveform or current pulses, and delivers the stimulation via an implantable medical lead 10 carrying an array of implantable stimulation electrodes 11. In some cases, multiple implantable leads may be provided. In the example of FIG. 1, a distal end of lead 10 is bifurcated and includes two lead segments 12A and 12B (collectively "lead segments 12"). Lead segments 12A and 12B each include a set of electrodes forming part of the array of electrodes 11. In various examples, lead segments 12A and 12B may each carry four, eight, twelve, sixteen, or more electrodes. In FIG. 1, each lead segment 12A, 12B carries four electrodes, configured as ring electrodes at different axial positions near the distal ends of the lead segments. Throughout the remainder of this disclosure, for purposes of simplicity, the disclosure may generally refer to electrodes carried on "leads" rather than "lead segments."

FIG. 1 further depicts a housing, or can, electrode 13. Housing electrode 13 may be formed integrally with an outer surface of hermetically-sealed housing 14 of implantable stimulator 4, also referred to in this disclosure as IMD 4, or otherwise coupled to housing 14. In one example, housing electrode 13 may be described as an active, non-detachable electrode on the surface of the IMD. In some examples, housing electrode 13 is defined by an uninsulated portion of an outward facing portion of housing 14 of IMD 4. Other divisions between insulated and uninsulated portions of housing 14 may be employed to define two or more housing electrodes, which may be referred to as case or can electrodes. In some examples, housing electrode 13 comprises substantially all of housing 14, one side of housing 14, a portion of the housing 14, or multiple portions of housing 14. In other examples, electrode 13 may be formed by an electrode on a dedicated short lead extending from housing 14. As a further alternative, housing electrode 13 could be provided on a proximal portion of one of the leads carrying electrodes 11. The proximal portion may be closely adjacent to housing 14, e.g., at or near a point at which lead 10 is coupled to the housing, such as adjacent to a lead connection header 8 of the housing. In another example, a patch electrode or other indifferent electrode may be attached externally to serve as the can or case.

In some examples, lead 10 may also carry one or more sense electrodes to permit implantable stimulator 4 to sense electrical signals from patient 6. Some of the stimulation electrodes may be coupled to function as stimulation electrodes and sense electrodes on a selective basis. In other examples, implantable stimulator 4 may be coupled to one or more leads which may or may not be bifurcated. In such examples, the leads may be coupled to implantable stimulator 4 via a common lead extension or via separate lead extensions.

A proximal end of lead 10 may be both electrically and mechanically coupled to header 8 on implantable stimulator 4 either directly or indirectly via a lead extension. Conductors in the lead body may electrically connect stimulation electrodes located on lead segments 12 to implantable stimulator 4. Lead 10 traverses from the implant region of implantable stimulator 4 along the neck of patient 6 to cranium 18 of patient 6 to access brain 16. Lead segments 12A and 12B are implanted within the right and left hemispheres, respectively, in order to deliver electrical stimulation to one or more regions of brain 16, which may be selected based on the patient condition or disorder.

Implantable stimulator 4 may deliver, for example, deep brain stimulation (DBS) or cortical stimulation (CS) therapy to patient 6 via the electrodes carried by, i.e., located on, lead segments 12 to treat any of a variety of neurological disorders or diseases. Example neurological disorders may include depression, dementia, obsessive-compulsive disorder and movement disorders, such as Parkinson's disease, spasticity, epilepsy, and dystonia. DBS also may be useful for treating other patient conditions, such as migraines and obesity. However, the disclosure is not limited to the configuration of lead 10 shown in FIG. 1, or to the delivery of DBS or CS therapy.

Lead segments 12A, 12B may be implanted within a desired location of brain 16 through respective holes in cranium 18. Lead segments 12A, 12B may be placed at any location within brain 16 such that the electrodes located on lead segments 12A, 12B are capable of providing electrical stimulation to targeted tissue during treatment. Example locations for lead segments 12A, 12B within brain 26 may include the pedunculopontine nucleus (PPN), thalamus, basal ganglia structures (e.g., globus pallidus, substantia nigra, subthalmic nucleus), zona inserta, fiber tracts, lenticular fasciculus (and branches thereof), ansa lenticularis, and/or the Field of Forel (thalamic fasciculus). In the case of migraines, lead segments 12 may be implanted to provide stimulation to the visual cortex of brain 16 in order to reduce or eliminate migraine headaches afflicting patient 6. However, the target therapy delivery site may depend upon the patient condition or disorder being treated.

The electrodes of lead segments 12A, 12B are shown as ring electrodes. Ring electrodes are commonly used in DBS applications because they are simple to program and are capable of delivering an electrical field to any tissue adjacent to lead segments 12A, 12B. In other implementations, the electrodes of lead segments 12A, 12B may have different configurations. For example, the electrodes of lead segments 12A, 12B may have a complex electrode array geometry that is capable of producing shaped electrical fields. The complex electrode array geometry may include multiple electrodes (e.g., partial ring or segmented electrodes) around the perimeter of each lead segments 12A, 12B, rather than one ring electrode. In this manner, electrical stimulation may be directed in a specific direction from lead segments 12 to enhance therapy efficacy and reduce possible adverse side effects from stimulating a large volume of tissue. In alternative examples, lead segments 12 may have shapes other than elongated cylinders as shown in FIG. 1. For example, lead segments 12 may be paddle leads, spherical leads, bendable leads, or any other type of shape effective in treating patient 6.

Therapy system 2 also may include a clinician programmer 20 and/or a patient programmer 22. Clinician programmer 20 may be a handheld computing device that permits a clinician to program stimulation therapy for patient 6 via a user interface, e.g., using input keys and a display. For example, using clinician programmer 20, the clinician may specify stimulation parameters, i.e., create programs, for use in delivery of stimulation therapy. Clinician programmer 20 may support telemetry (e.g., radio frequency (RF) telemetry) with implantable stimulator 4 to download programs and, optionally, upload operational or physiological data stored by implantable stimulator 4. In this manner, the clinician may periodically interrogate implantable stimulator 4 to evaluate efficacy and, if necessary, modify the programs or create new programs. In some examples, clinician programmer 20 transmits programs to patient programmer 22 in addition to or instead of implantable stimulator 4. In some examples, patient programmer 22 may serve as the clinician programmer.

Like clinician programmer 20, patient programmer 22 may be a handheld computing device. Patient programmer 22 may also include a display and input keys to allow patient 6 to interact with patient programmer 22 and implantable stimulator 4. In this manner, patient programmer 22 provides patient 6 with a user interface for control of the stimulation therapy delivered by implantable stimulator 4. For example, patient 6 may use patient programmer 22 to start, stop or adjust electrical stimulation therapy. In particular, patient programmer 22 may permit patient 6 to adjust stimulation parameters of a program such as duration, current or voltage amplitude, pulse width and pulse rate. Patient 6 may also select a program, e.g., from among a plurality of stored programs, as the present program to control delivery of stimulation by implantable stimulator 4.

Clinician programmer 20 and/or patient programmer 22 may be used to define stimulation therapy parameters for one or more leads or to graphically define desired stimulation field(s) within zones on or adjacent to one or more leads, and generate the stimulation required to create the stimulation field. In particular, clinician programmer 20 and/or patient programmer 22 may be used for translating one or more user input stimulation zones into a set of electrodes for delivering electrical stimulation therapy to a patient, determining the variable electrical stimulation contributions of each electrode to the zone, and determining amplitudes of electrical stimulation when using zone-based programming. Clinician programmer 20 and/or patient programmer 22 may also be used for graphically representing the stimulation zone and receiving input from a user that manipulates the shape and position of the zone. In one example, clinician programmer 20 may be used to define and store one or more programs to target a specific zone with different parameters. The programs may be grouped so that a user may more easily select a group of programs to be active simultaneously. In one example, the programs may be grouped according to the zones targeted by the therapy, e.g., back or right leg, etc., so that a user may select the program most appropriate for the patient. In some examples, clinician programmer 20 may be used to define stimulation therapy by defining parameters for one or more electrodes.

In some examples, implantable stimulator 4 delivers stimulation according to a group of programs at a given time. Each program of such a program group may include respective values for each of a plurality of therapy parameters, such as respective values for each of current or voltage amplitude, pulse width, pulse shape, pulse rate and electrode configuration (e.g., electrode combination and polarity). Implantable stimulator 4 may interleave pulses or other signals according to the different programs of a program group, e.g., cycle through the programs, to simultaneously treat different symptoms or different body regions, or provide a combined therapeutic effect. In such examples, clinician programmer 20 may be used to create programs, and assemble the programs into program groups. Patient programmer 22 may be used to adjust stimulation parameters of one or more programs of a program group, and select a program group, e.g., from among a plurality of stored program groups, as the current program group to control delivery of stimulation by implantable stimulator 4.

Implantable stimulator 4, clinician programmer 20, and patient programmer 22 may communicate via cables or a wireless communication, as shown in FIG. 1. Clinician programmer 20 and patient programmer 22 may, for example, communicate via wireless communication with implantable stimulator 4 using RF telemetry techniques known in the art or other standard communication protocols such as, for example, Bluetooth®. Clinician programmer 20 and patient programmer 22 also may communicate with each other using any of a variety of wireless communication techniques, such as RF communication according to the 802.11 or Bluetooth® specification sets, infrared communication, e.g., according to the IrDA standard, or other standard or proprietary telemetry protocols. Each of clinician programmer 20 and patient programmer 22 may include a transceiver to permit bi-directional communication with implantable stimulator 4.

Generally, system 2 delivers stimulation therapy to patient 6 in the form of constant current or voltage waveforms or constant current or voltage pulses. The shapes of the pulses may vary according to different design objectives. In the case of current-based stimulation, implantable stimulator 4 regulates current that is sourced or sunk by one or more electrodes, referred to as regulated electrodes. In some examples, one of the electrodes may be unregulated. In such configurations, either the housing electrode or a lead electrode may be the unregulated electrode. Alternatively, all active electrodes may be regulated, i.e., coupled to a current regulator such as a regulated current source or sink.

A source current may refer to a current that flows out of an electrode, e.g., from a regulated current source via a regulated current path to surrounding tissue, or from a reference voltage via an unregulated current path. A sink current may refer to a current that flows into an electrode, e.g. from surrounding tissue and is sunk by a regulated current sink via a regulated current path or by a reference voltage via an unregulated current path. Regulated source currents may sum to produce a greater overall source current. Regulated sink currents may sum to produce a greater overall sink current. Regulated source and regulated sink currents may partially or entirely cancel one another, producing a net difference in the form of a net source current or sink current in the case or partial cancellation. An unregulated current path can source or sink current approximately equal to this net difference.

Figure 2:
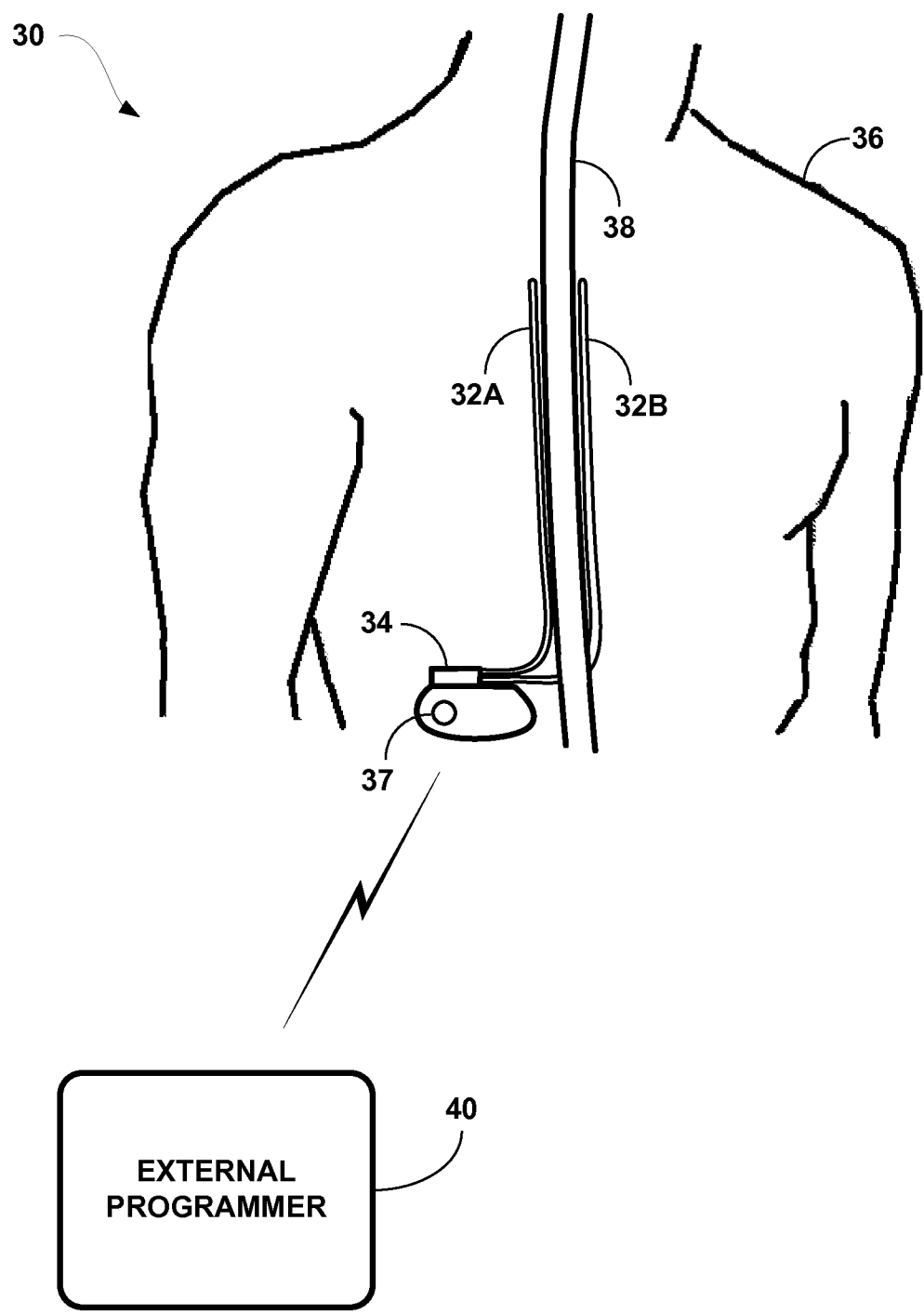
FIG. 2 is a conceptual diagram illustrating another example therapy system that includes an implantable stimulator coupled to a stimulation lead.

FIG. 2 is a conceptual diagram illustrating system 30 that delivers stimulation therapy to spinal cord 38 of patient 36. Other electrical stimulation systems may be configured to deliver electrical stimulation to gastrointestinal organs, pelvic nerves or muscle, peripheral nerves, or other stimulation sites. In the example of FIG. 2, system 30 delivers stimulation therapy from implantable stimulator 34 to spinal cord 38 via one or more electrodes (not shown) carried by, i.e., located on, implantable medical leads 32A and 32B (collectively "leads 32") as well as the housing of implantable stimulator 34, e.g., housing electrode 37. System 30 and, more particularly, implantable stimulator 34 may operate in a manner similar to implantable stimulator 4 (FIG. 1). That is, in a current-based example, implantable stimulator 34 delivers controlled current stimulation pulses or waveforms to patient 36 via one or more regulated, stimulation electrodes. Alternatively, implantable stimulator 34 may be configured to deliver constant voltage pulses. As mentioned above, in some examples, one of the electrodes may be unregulated.

In the example of FIG. 2, the distal ends of leads 32 carry electrodes that are placed adjacent to the target tissue of spinal cord 38. The proximal ends of leads 32 may be both electrically and mechanically coupled to implantable stimulator 34 either directly or indirectly via a lead extension and header. Alternatively, in some examples, leads 32 may be implanted and coupled to an external stimulator, e.g., through a percutaneous port. In additional example implementations, stimulator 34 may be a leadless stimulator with one or more arrays of electrodes arranged on a housing of the stimulator rather than leads that extend from the housing. Application of certain techniques will be described in this disclosure with respect to implantable stimulator 34 and implantable leads 32 having ring electrodes for purposes of illustration. However, other types of electrodes may be used.

Stimulator 34 may be implanted in patient 36 at a location minimally noticeable to the patient. For SCS, stimulator 34 may be located in the lower abdomen, lower back, or other location to secure the stimulator. Leads 32 may be tunneled from stimulator 34 through tissue to reach the target tissue adjacent to spinal cord 38 for stimulation delivery. At the distal ends of leads 32 are one or more electrodes (not shown) that transfer the stimulation pulses from the lead to the tissue substantially simultaneously with stimulation pulses. Some of the electrodes may be electrode pads on a paddle lead, circular (i.e., ring) electrodes surrounding the body of leads 32, conformable electrodes, cuff electrodes, segmented electrodes, or any other type of electrodes capable of forming unipolar, bipolar or multi-polar electrode configurations.

The stimulation pulses may be delivered using various electrode arrangements such as unipolar arrangements, bipolar arrangements or multipolar arrangements. A unipolar stimulation arrangement generally refers to the use of an anode on the housing that sources current and one or more cathodes on one or more leads that sink current. A bipolar stimulation arrangement generally refers to the use of an anode on a lead that sources current and a cathode on the same lead and/or another lead that sink current. A multipolar stimulation arrangement generally refers to the use of more than one anode on a lead that each sources current and one or more cathodes on the same lead or another lead that sink current, or the use of one anode on a lead that sources current and multiple cathodes on the same lead or another lead that sink current. A hybrid stimulation arrangement that combines both unipolar and bipolar electrode relationships may be referred to as an omnipolar arrangement. In an omnipolar arrangement, an anode on the housing may be used to deliver stimulation pulses substantially simultaneously with at least one anode on a lead and at least one cathode on a lead. In this case, for an omnipolar arrangement, at least one anode on a lead and at least one anode on the housing can be used simultaneously in combination with at least one cathode on a lead. In other omnipolar arrangements, a cathode on the housing may be used to deliver stimulation pulses substantially simultaneously with at least one cathode on a lead and at least one anode on a lead. In this alternative case, for an omnipolar arrangement, at least one cathode on a lead and at least one cathode on the housing can be used simultaneously in combination with at least one anode on a lead. Any of the above electrode arrangements, or other electrode arrangements, may be used to deliver electrical stimulation in accordance with techniques described in this disclosure.

Implantable stimulator 34 delivers stimulation to spinal cord 38 to reduce the amount of pain perceived by patient 36. As mentioned above, however, the stimulator may be used with a variety of different therapies, such as peripheral nerve stimulation (PNS), peripheral nerve field stimulation (PNFS), deep brain stimulation (DBS), cortical stimulation (CS), pelvic floor stimulation, peripheral nerve stimulation, gastric stimulation, and the like. The stimulation delivered by implantable stimulator 34 may take the form of stimulation pulses or continuous stimulation waveforms, and may be characterized by controlled current or voltage levels, as well as programmed pulse widths and pulse rates in the case of stimulation current pulses. Stimulation may be delivered via selected combinations of electrodes located on one or both of leads 32 and on the housing. Stimulation of spinal cord 38 may, for example, prevent pain signals from traveling through the spinal cord and to the brain of the patient. Patient 34 perceives the interruption of pain signals as a reduction in pain and, therefore, efficacious therapy.

With reference to FIG. 2, a user, such as a clinician or patient 36, may interact with a user interface of external programmer 40 to program stimulator 34. Programming of stimulator 34 may refer generally to the generation and transfer of commands, programs, or other information to control the operation of the stimulator. For example, programmer 40 may transmit programs, parameter adjustments, program selections, group selections, or other information to control the operation of stimulator 34, e.g., by wireless telemetry. In accordance with this disclosure, programmer 40 may transmit to the stimulator 34 information regarding the patient and regarding therapy the patient received during previous sessions including, for example, images that show placement of leads 32.

In some cases, external programmer 40 may be characterized as a physician or clinician programmer, such as clinician programmer 20 (FIG. 1), if it is primarily intended for use by a physician or clinician. In other cases, external programmer 40 may be characterized as a patient programmer, such as patient programmer 22 (FIG. 1), if it is primarily intended for use by a patient. In general, a physician or clinician programmer may support selection and generation of programs by a clinician for use by stimulator 34, whereas a patient programmer may support adjustment and selection of such programs by a patient during ordinary use.

Whether programmer 40 is configured for clinician or patient use, programmer 40 may communicate to implantable stimulator 34 or any other computing device via wireless communication. Programmer 40, for example, may communicate via wireless communication with implantable stimulator 34 using radio frequency (RF) telemetry techniques known in the art or other communication standards such as, for example, Bluetooth®. Programmer 40 may also communicate with another programmer or computing device via a wired or wireless connection using any of a variety of local wireless communication techniques, such as RF communication according to the 802.11 or Bluetooth® specification sets, infrared communication according to the IRDA specification set, or other standard or proprietary telemetry protocols. Programmer 40 may also communicate with another programming or computing device via exchange of removable media, such as magnetic or optical disks, or memory cards or sticks. Further, programmer 40 may communicate with implantable stimulator 34 and other programming devices via remote telemetry techniques known in the art, communicating via a local area network (LAN), wide area network (WAN), public switched telephone network (PSTN), or cellular telephone network, for example.

In one example, programming of stimulator 34 may be done by programming therapy parameters for one or more electrodes. The therapy parameters may be, for example, pulse width, current amplitude, pulse rate, etc. In another example, programming of stimulator 34 may also include graphically defining a desired stimulation field(s) within zones on or adjacent to one or more leads or electrodes, and generating, via a programmer, the current stimulation required to create the stimulation field. Programming of stimulator 34 may also include translating one or more user input stimulation zones into a set of electrodes for delivering electrical stimulation therapy to a patient, and a set of parameters such as pulse current amplitudes associated with such electrodes. Programming may further include manipulating the shape and position of the zone, including behaviors of the zone while moving and when colliding with other zones or system interlocks. As the stimulation zone is sized, moved, or shaped, the programmer may automatically compute updated electrode selections and parameters for delivery of stimulation indicated by the stimulation zone.

Although the disclosure generally refers to implantable stimulators for purposes of illustrations, techniques described in this disclosure also may be used with respect to images of implant regions associated with other types of IMDs, including implantable fluid delivery devices, such as insulin pumps, intra-thecal drug delivery pumps, or other devices that deliver medication or other fluids via one or more fluid delivery elements such as catheters. Such devices may provide fluid delivery therapy for chronic pain, diabetes, or any of a variety of other disorders. In each case, the device may include one or more therapy delivery elements such as one or more catheters implanted within a therapy region. In some cases, a pump may be fully implantable or may be an external device coupled to one or more percutaneously implanted catheters that extend into a therapy region. Accordingly, description of implantable stimulators is provided for purposes of illustration and should not be considered limiting of the techniques as broadly described in this disclosure.

Figure 3:
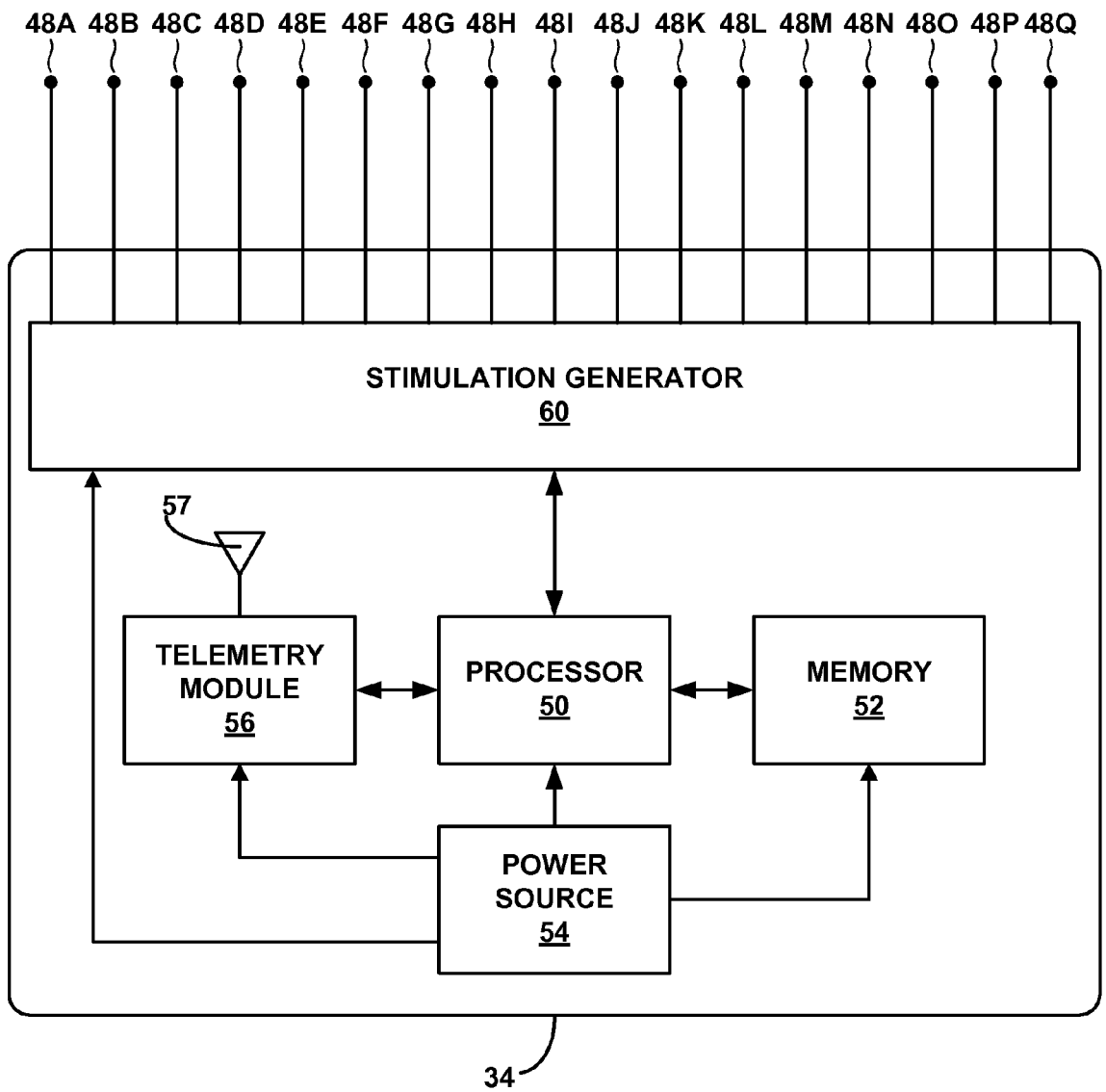
FIG. 3 is a block diagram illustrating various example components of an implantable electrical stimulator.

FIG. 3 is a block diagram illustrating various components of an example implantable stimulator 34. Although the components shown in FIG. 3 are described in reference to implantable stimulator 34, the components may also be included within implantable stimulator 4 shown in FIG. 1 and used within system 2. In the example of FIG. 3, implantable stimulator 34 includes processor 50, memory 52, power source 54, telemetry module 56, antenna 57, and a stimulation generator 60. Implantable stimulator 34 is also shown in FIG. 3 coupled to electrodes 48A-Q (collectively "electrodes 48"). Electrodes 48A-48P are implantable and may be deployed on one or more implantable leads. With respect to FIG. 1, lead segments 12A and 12B may carry electrodes 48A-H and electrodes 48I-48P, respectively. In some cases, one or more additional electrodes may be located on or within the housing of implantable stimulator 34, e.g., to provide a common or ground electrode or a housing anode. With respect to FIG. 2, leads 32A and 32B may carry electrodes 48A-H and electrodes 48I-P, respectively. In the examples of FIGS. 1 and 2, a lead or lead segment carries eight electrodes to provide an 2×8 electrode configuration (two leads with 8 electrodes each), providing a total of sixteen different electrodes. The leads may be detachable from a housing associated with implantable stimulator 34, or be fixed to such a housing.

In other examples, different electrode configurations comprising a single lead, two leads, three leads, or more may be provided. In addition, electrode counts on leads may vary and may be the same or different from a lead to lead. Examples of other configurations include one lead with eight electrodes (1×8), one lead with 12 electrodes (1×12), one lead with 16 electrodes (1×16), two leads with four electrodes each (2×4), three leads with four electrodes each (3×4), three leads with eight electrodes each (3×8), three leads with four, eight, and four electrodes, respectively (4-8-4), two leads with 12 or 16 electrodes (2×12, 2×16), or other configurations. Different electrodes are selected to form electrode combinations. Polarities are assigned to the selected electrodes to form electrode configurations.

Electrode 48Q represents one or more electrodes that may be carried on a housing, i.e., can, of implantable stimulator 4. Electrode 48Q may be configured as a regulated or unregulated electrode for use in an electrode configuration with selected regulated and/or unregulated electrodes among electrodes 48A-48P, which may be located on a lead body of one or more leads, as described above. Electrode 48Q may be formed together on a housing that carries the electrode and houses the components of implantable stimulator 4, such as stimulation generator 60, processor 50, memory 52, telemetry module 56, and power source 54.

Housing electrode 48Q may be configured for use as an anode to source current substantially simultaneously with current sourced by one or more other electrodes 48A-48P to form a unipolar or omnipolar electrode arrangement. By way of specific example, in an omnipolar arrangement, electrodes 48A, 48B, and housing electrode 48Q each could be configured for use as anodes. Electrodes 48A, 48B could deliver electrical stimulation current substantially simultaneously with the electrical stimulation current delivered via housing electrode 48Q. In this illustration, one or more cathodes could be formed with other electrodes (e.g., any of electrodes 48C-48P) on the leads to sink current sourced by anodes 48A, 48B and 48Q. Any of a variety of electrode arrangements such as unipolar, bipolar, multipolar, or omnipolar arrangements may be used to deliver stimulation. Accordingly, discussion of particular arrangements are provided for purposes of illustration, which should not be considered limiting of the techniques broadly described in this disclosure.

Memory 52 may store instructions for execution by processor 50, stimulation therapy data, sensor data, and/or other information regarding therapy for patient 6. Processor 50 may control stimulation generator 60 to deliver stimulation according to a selected one or more of a plurality of programs or program groups stored in memory 52. Memory 52 may include any electronic data storage media, such as random access memory (RAM), read-only memory (ROM), electronically-erasable programmable ROM (EEPROM), flash memory, or the like. Memory 52 may store program instructions that, when executed by processor 50, cause the processor to perform various functions ascribed to processor 50 and implantable stimulator 4 in this disclosure.

In accordance with the techniques described in this disclosure, information stored on the memory 52 may include information regarding therapy that the patient 6 had previously received or information regarding a current therapy. Storing such information may be useful for subsequent therapy such that, for example, a clinician may retrieve the stored information to determine the therapy applied to the patient during a previous therapy session, in accordance with this disclosure. The information stored in the memory 52 may be, for example, an image captured and transferred by wireless telemetry into the implantable stimulator 34 by a programmer, such as clinician programmer 20. As an example, the image may be obtained during an in-clinic programming session, and may show, for example, lead configuration and placement within a patient's anatomical implant region, in accordance with this disclosure. The implant region may be any of several anatomical regions of patient in which one or more leads may be implanted for delivery of therapy, including the spinal cord, the occipital region, the brain, the pelvic floor, the heart, the gastrointestinal tract, one or more limbs, or the like.

The programmer may obtain the image by capturing a photograph of a hard copy or electronic display presenting an image obtained by a diagnostic medical imaging device, such as a fluoroscopic imaging or other x-ray imaging device, a magnetic resonance imaging (MRI) device, a positron emission tomography (PET) device, a computer tomography (CT) device, an ultrasonic imaging device, electrical impedance topography, or other imagine devices. For example, the programmer may include an integrated digital camera or may be coupled to a digital camera, by a wired or wireless communication medium. Alternatively, the programmer may obtain the image electronically from an imaging device, a network storage server, a removable storage medium such as Flash memory, or other devices. In each case, the image may be stored at least temporarily on the programmer, permitting viewing, manipulation, compression, or editing of the image. In some examples, a user may manipulate, compress, or edit the image to produce an image suitable or desirable for transferring to the IMD for storage. In other examples, the programmer may automatically manipulate, compress, or edit the image to produce a version suitable for transfer to the IMD. Also, in some examples, the IMD may store multiple images, e.g., from different perspectives, or with different views, such as different zoom factors, cropping, spatial resolution, image density resolution or the like. In one example, the IMD may be used to deliver therapy to multiple regions in the patient, and may store images associated with the different implant regions.

The image may be subsequently retrieved from the IMD, either by a patient programmer or clinician programmer, or both, for any of several reasons such as, for example, later viewing, or subsequent programming and/or therapy delivery to the region associated with the image. In some cases, storing the image in an IMD will permit a clinician to retrieve and transfer the image and thereby view the image without the requirement for storage of the image in the clinic or on the programmer. Rather, the clinician may use a different programmer, or the patient may visit a different clinic, and the image may be used to determine the previous therapy provided to the patient. In each case, the image may be accessed for review and verification of lead configuration because it is conveniently stored in the IMD, which may usually be with the patient. In some cases, the image may alternatively or additionally be stored on a patient programmer, which is ordinarily with the patient. However, storing the image in the IMD may ensure that the image can be accessed by an external programmer whenever the patient is present, e.g., whenever the patient visits a clinic for a programming session or other evaluation. In one example, a user may retrieve and print the image. In this example, the user may be able to optionally print a composite image, which may include the image and image information such as, for example, annotations made by a user, lead orientation changes, and other changes a user might have made to the image before storing it. The user may print images of a session in the form of a session report for the patient for archival and future reference. The reports for a patient may be stored at a location, e.g., on a system-wide storage device or at a URL, where other user may be able to access stored reports for subsequent sessions and therapy. In one example, a personalized image associated with the patient may be stored on the IMD. In this example, when a user turns on a programmer, the programmer may retrieve the personalized image and display it on the programmer screen as a background. The personalized image may be, for example, an image of the patient, an image selected by the patient, or the like.

Processor 50 may include one or more microprocessors, digital signal processors (DSPs), application-specific integrated circuits (ASICs), field-programmable gate arrays (FPGAs), or other digital logic circuitry. Processor 50 controls operation of implantable stimulator 34, e.g., controls stimulation generator 60 to deliver stimulation therapy according to a selected program or group of programs retrieved from memory 52. For example, processor 50 may control stimulation generator 60 to deliver electrical signals, e.g., as stimulation pulses or continuous waveforms, with current amplitudes, pulse widths (if applicable), and rates specified by one or more stimulation programs. Processor 50 may also control stimulation generator 60 to selectively deliver the stimulation via subsets of electrodes 48, also referred to as electrode combinations, and with polarities specified by one or more programs.

Upon selection of a particular program or program group, processor 50 may control stimulation generator 60 to deliver stimulation according to the selected program or programs in the groups, e.g., simultaneously or on a time-interleaved basis. A group may include a single program or multiple programs. As mentioned previously, each program may specify a set of stimulation parameters, such as amplitude, pulse width and pulse rate, if applicable. For a continuous waveform, parameters may include amplitude and frequency. In addition, each program may specify a particular electrode combination for delivery of stimulation, and an electrode configuration in terms of the polarities and regulated/unregulated status of the electrodes. The electrode combination may specify particular electrodes in a single array or multiple arrays, and on a single lead or among multiple leads.

Stimulation generator 60 is electrically coupled to electrodes 48A-P via conductors of the respective lead, such as lead 12 in FIG. 1 or leads 32 in FIG. 2, in implementations in which electrodes 48A-P are carried by, located on, leads. Stimulation generator 60 may be electrically coupled to one or more housing ("can") electrodes 48Q via an electrical conductor disposed within the housing of implantable stimulator 4 (FIG. 1) or implantable stimulator 34 (FIG. 3). A housing electrode 48Q may be configured as a regulated or unregulated electrode to form an electrode configuration in conjunction with one or more of electrodes 48A-48P located on leads of the IMD. Housing electrode 48Q may be configured for use as an anode to source current substantially simultaneously with one or more electrodes, e.g., any of electrodes 48A-48P, on one or more leads configured for use as anodes.

Stimulation generator 60 may include stimulation generation circuitry to generate stimulation pulses or waveforms and circuitry for switching stimulation across different electrode combinations, e.g., in response to control by processor 50. Stimulation generator 60 produces an electrical stimulation signal in accordance with a program based on control signals from processor 50.

For example, stimulation generator 60 may include a charging circuit that selectively applies energy from power source 54 to a capacitor module for generation and delivery of a supply voltage for generation of stimulation signal. In addition to capacitors, the capacitor module may include switches. In this manner, the capacitor module may be configurable, e.g., based on signals from processor 50, to store a desired voltage for delivery of stimulation at a voltage or current amplitude specified by a program. For delivery of stimulation pulses, switches within the capacitor module may control the widths of the pulses based on signals from processor 50.

Telemetry module 56 may include a radio frequency (RF) transceiver to permit bi-directional communication between implantable stimulator 34 and each of clinician programmer 20 and patient programmer 22. In one example, telemetry module 56 may utilize other communication protocols and a corresponding transceiver, for example, a Bluetooth® transceiver for telemetry using the Bluetooth® protocol. Telemetry module 56 may include an antenna 57 that may take on a variety of forms. For example, antenna 57 may be formed by a conductive coil or wire embedded in a housing associated with medical device 4. Alternatively, antenna 57 may be mounted on a circuit board carrying other components of implantable stimulator 34 or take the form of a circuit trace on the circuit board. In this way, telemetry module 56 may permit communication with clinician programmer 20 and patient programmer 22 in FIG. 1 or external programmer 40 in FIG. 2, to receive, for example, new programs or program groups, or adjustments to programs or program groups.

Telemetry module 56 may also permit communication with clinician programmer 20 to receive, for example, an image captured by the programmer of the lead placement along with information regarding the captured image and the therapy received by the patient during previous sessions, in accordance with this disclosure. Telemetry module 56 may also communicate information regarding previous therapy sessions that have been stored in memory 52, to an external programmer during a subsequent therapy session. In one example, the information regarding a previous therapy session may have been imported by a programmer used in the previous session. In another example, information regarding a previous therapy session may include earlier versions of a lead placement image, e.g., during trial screening or immediately post implant, where comparison between information from a previous session and a current one may be useful in detecting lead migration or other clinical changes. The stored information may, for example, include an image of the placement of leads during the previous session with corresponding metadata and/or information regarding the patient, clinic(s) where the patient received previous treatments, previous clinician information, etc. In some examples, a user may look at images of the leads in one region over a span of a time period to determine a trending pattern of lead placement for a patient over time. In other example, a user may look at images of the leads over a span of a time period for multiple patients who may be receiving the same therapy and/or may have implant patterns that are similar.

Power source 54 may be a non-rechargeable primary cell battery or a rechargeable battery and may be coupled to power circuitry. However, the disclosure is not limited to examples in which the power source is a battery. In another example, as an example, power source 54 may comprise a supercapacitor. In some examples, power source 54 may be rechargeable via induction or ultrasonic energy transmission, and include an appropriate circuit for recovering transcutaneously received energy. For example, power source 54 may be coupled to a secondary coil and a rectifier circuit for inductive energy transfer. In additional examples, power source 54 may include a small rechargeable circuit and a power generation circuit to produce the operating power. Recharging may be accomplished through proximal inductive interaction between an external charger and an inductive charging coil within stimulator 4. In some examples, power requirements may be small enough to allow stimulator 4 to utilize patient motion at least in part and implement a kinetic energy-scavenging device to trickle charge a rechargeable battery. A voltage regulator may generate one or more regulated voltages using the battery power.

Figure 4:
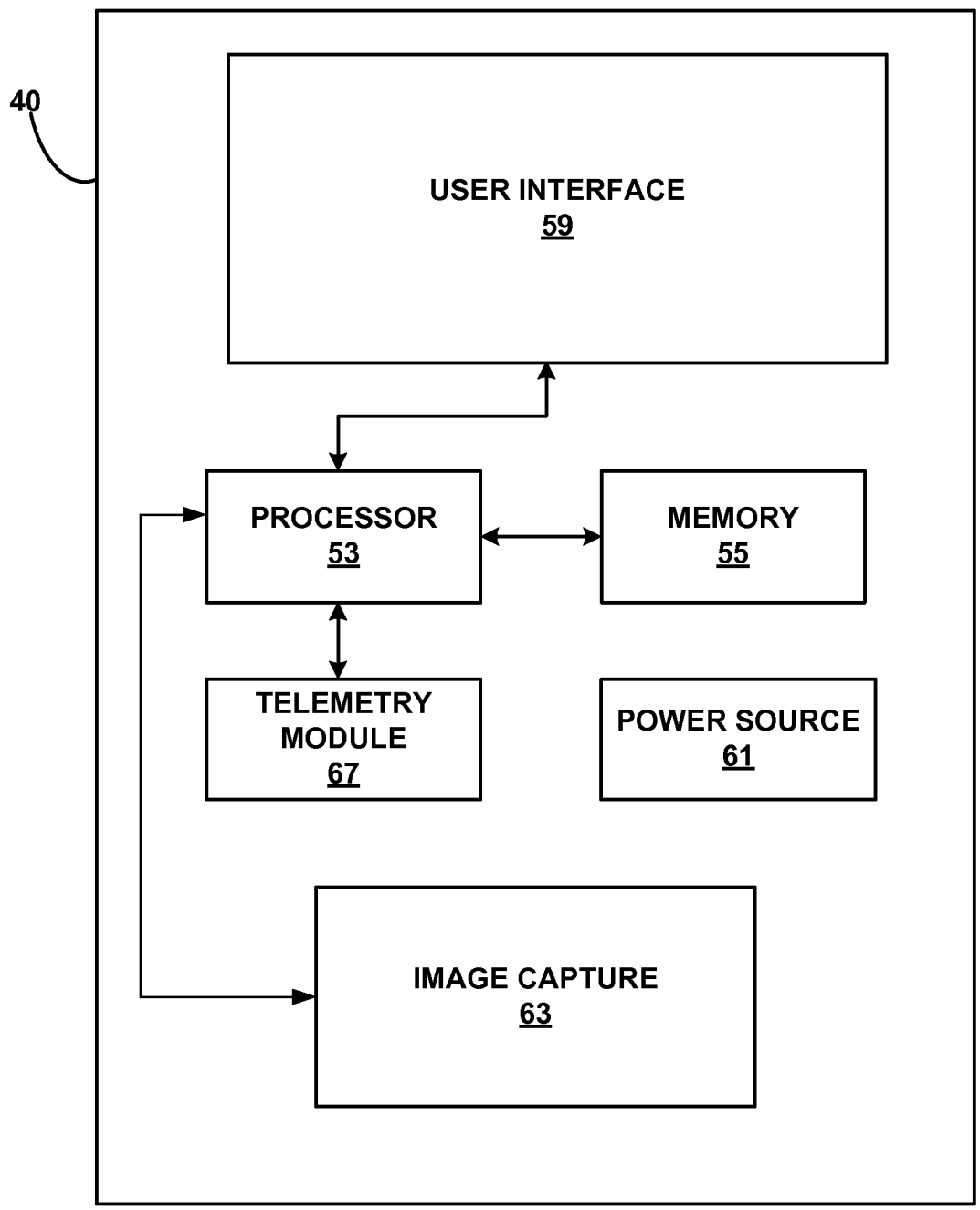
FIG. 4 is a block diagram illustrating various example components of an external programmer.

FIG. 4 is a functional block diagram illustrating various components of an external programmer 40 for an implantable stimulator 14. Although the components shown in FIG. 4 are described in reference to external programmer 40, the components may also be included within clinician programmer 20 or patient programmer 22 shown in FIG. 1. As shown in FIG. 4, external programmer 40 includes processor 53, memory 55, telemetry module 67, user interface 59, and power source 61. In general, processor 53 controls user interface 59, stores and retrieves data to and from memory 55, and controls transmission of data with implantable stimulator 34 through telemetry module 67. Processor 53 may take the form of one or more microprocessors, controllers, DSPs, ASICS, FPGAs, or equivalent discrete or integrated logic circuitry. The functions attributed to processor 53 herein may be embodied as software, firmware, hardware or any combination thereof.

Memory 55 may store instructions that cause processor 53 to provide various aspects of the functionality ascribed to external programmer 40 herein. Memory 55 may include any fixed or removable magnetic, optical, or electrical media, such as RAM, ROM, CD-ROM, magnetic disks, EEPROM, or the like. Memory 55 may also include a removable memory portion that may be used to provide memory updates or increases in memory capacities. A removable memory may also allow patient data to be easily transferred to another computing device, or to be removed before programmer 40 is used to program therapy for another patient. Memory 55 may also store information that controls operation of implantable stimulator 4, such as therapy delivery values.

In accordance with the techniques described in this disclosure, the external programmer 40 may also include an image capturing device 63. The image capturing device 63 may be built into the external programmer 40 or may be connected to the external programmer 40 via an interface using a wired or wireless connection. The processor 53 may control the image capturing device 63 to capture images as specified by the user of the external programmer 40 and may manipulate the captured images, as will be described in more detail below. In some examples, image capturing device 63 may be a digital camera or web camera integrated with or coupled to programmer 40 to capture digital photographs of images presented on hardcopy media, such as film or paper, or a digital image display screen. Alternatively, the programmer may obtain the image electronically from an imaging device, a network storage server, a removable storage medium such as Flash memory, or other devices, directly or over a network.

A clinician or patient 36 interacts with user interface 59 in order to, for example, manually select, change, or modify programs, e.g., by adjusting voltage or current amplitude, adjusting pulse rate, adjusting pulse width, or selecting different electrode combinations or configurations, and may provide efficacy feedback, or view stimulation data. User interface 59 may include a screen and one or more input buttons that allow external programmer 40 to receive input from a user. The screen may be, for example, a liquid crystal display (LCD), plasma display, organic light emitting diode (OLED), electrophoretic displays, dot matrix display, or touch screen. The input buttons may include a touch pad, increase and decrease buttons, emergency shut off button, and other input media needed to control the stimulation therapy.

Using the techniques of this disclosure, a clinician or patient 36 may graphically define desired stimulation regions using interface 59, and may capture an image of the stimulated regions and the placement of the leads that stimulate the regions using the image capturing device 63. The clinician or patient 36 may utilize, for example, the user interface 59 to control the image capturing device 63 to obtain an image and to manipulate the image, as will be described in more detail below. In one example, the clinician or patient may utilize the image capturing device 63 directly to obtain the image.

Telemetry module 67 allows the transfer of data to and from stimulator 34. Telemetry module 67 may communicate automatically with stimulator 34 at a scheduled time or when the telemetry module detects the proximity of the stimulator. Alternatively, telemetry module 67 may communicate with stimulator 34 when signaled by a user through user interface 59. To support RF communication, telemetry module 44 may include appropriate electronic components, such as amplifiers, filters, mixers, encoders, decoders, and the like. In other examples, telemetry module 67 may employ other communication standards such as, for example, Bluetooth® and telemetry module 67 may include the appropriate Bluetooth® components.

Programmer 40 may communicate wirelessly with implantable stimulator 34 using, for example, RF communication or proximal inductive interaction or other communication standards such as, for example, Bluetooth®. This wireless communication is possible through the use of telemetry module 67 which may be coupled to an internal antenna or an external antenna. Telemetry module 67 may be similar to telemetry module 57 of implantable stimulator 34. In accordance with this disclosure, programmer 40 may communicate images captured by the image capturing device 63 to implantable stimulator 34 via telemetry module 67. Additionally, programmer 40 may retrieve images previously stored on implantable stimulator 34 for viewing and/or manipulation by a user via user interface 59.

Programmer 40 may also be configured to communicate with another computing device via wireless communication techniques, or direct communication through a wired, e.g., network, connection. Examples of local wireless communication techniques that may be employed to facilitate communication between programmer 24 and another computing device include RF communication based on the 802.11 or Bluetooth® specification sets, infrared communication, e.g., based on the IrDA standard.

Power source 61 delivers operating power to the components of programmer 40. Power source 61 may be a rechargeable battery, such as a lithium ion or nickel metal hydride battery. Other rechargeable or conventional batteries may also be used. In some cases, external programmer 40 may be used when coupled to an alternating current (AC) outlet, i.e., AC line power, either directly or via an AC/DC adapter. Power source 61 may include circuitry to monitor power remaining within a battery. In this manner, user interface 59 may provide a current battery level indicator or low battery level indicator when the battery needs to be replaced or recharged. In some cases, power source 61 may be capable of estimating the remaining time of operation using the current battery.

Figure 5:
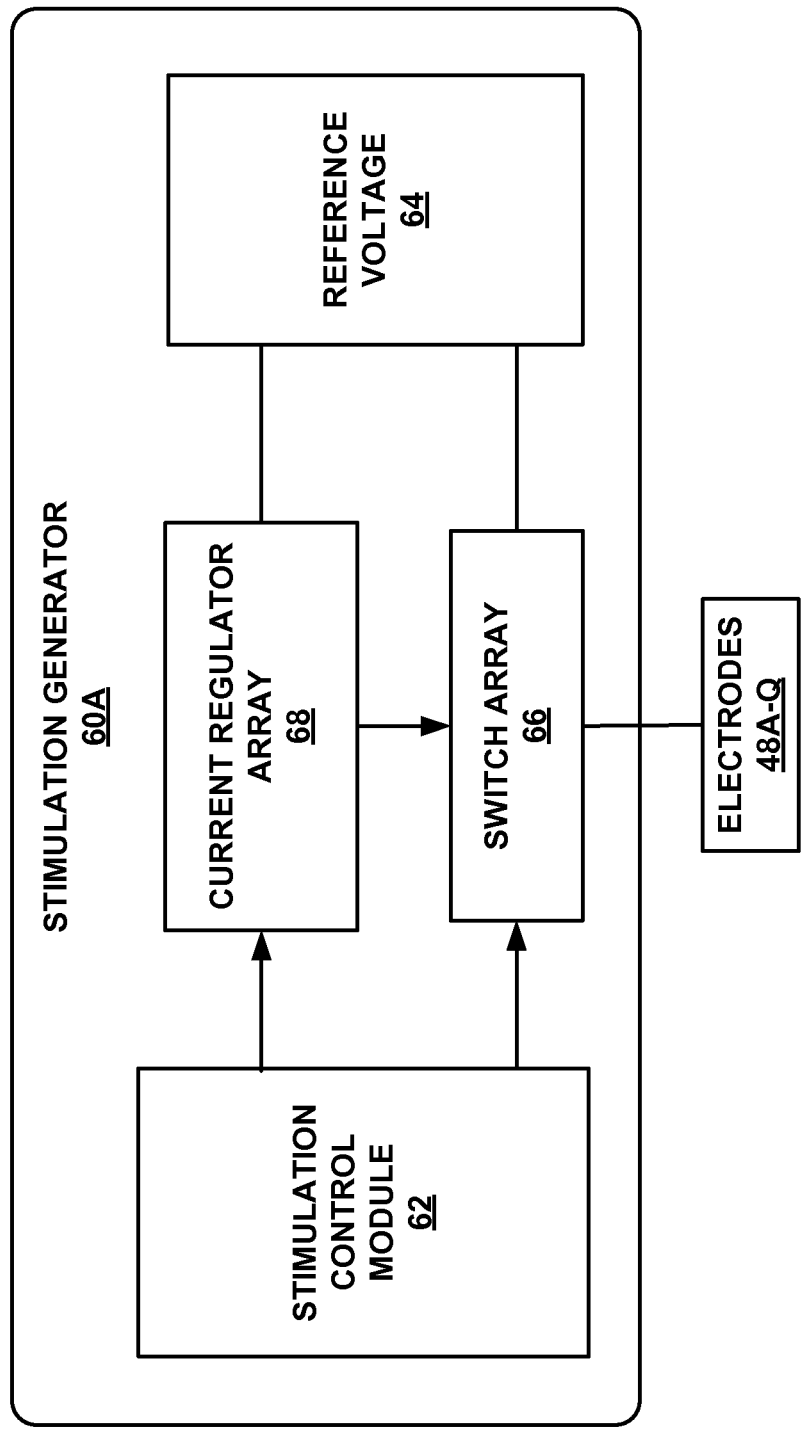
FIG. 5 is a block diagram illustrating various components of an example electrical stimulation generator for use in the implantable electrical stimulator of FIG. 3.

FIG. 5 is a block diagram illustrating various components of an example stimulation generator 60A. Stimulation generator 60A may be used with an implantable stimulator, e.g., to perform the functions of stimulation generator 60 as described with reference to FIGS. 1-3. Although described with respect to implantable stimulator 4, stimulation generator 60A may also be used for implantable stimulator 34, or other types of stimulators. In the example of FIG. 5, stimulation generator 60A is selectively, e.g., based on a signal from processor 50 (FIG. 3), configured to deliver constant current stimulation pulses to patient 6 via various electrode combinations. However, the disclosure is not limited to examples in which regulated current pulses are delivered. In other examples, stimulation generator 60A may provide continuous, regulated current waveforms, rather than regulated current pulses. In still other examples, stimulation generator 60A may deliver combinations or continuous waveforms and pulses, or selectively deliver either continuous waveforms or pulses. Stimulation generator 60A may generate either constant current-based or constant voltage-based stimulation in the form of pulses or continuous waveforms. In yet other examples, stimulation generator 60A may user a voltage regulator instead of a current regulator.

In the example illustrated in FIG. 5, stimulation generator 60A includes stimulation control module 62, reference voltage source 64, switch array 66, and current regulator array 68. Reference voltage source 64 may provide operating power to current regulator array 68, and may include a regulated voltage that sets the level of the reference voltage. As shown in FIG. 5, reference voltage source 64 may be coupled to provide operating power for the current regulator array 68 and provide a reference voltage for connection to electrodes 48A-48Q for an unregulated mode of electrode operation. In other examples, however, the voltage level of the reference voltage and the operating voltage level provided to regulated current source array 68 may be different.

Stimulation control module 62 forms a stimulation controller that controls switch array 66 and current regulator array 68 to deliver stimulation via electrodes 48A-48Q. Stimulation control module 62 may include one or more microprocessors, microcontrollers, digital signal processors (DSPs), application-specific integrated circuits (ASICs), field-programmable gate arrays (FPGAs), or other integrated or discrete logic circuitry. In operation, stimulation control module 62 may control delivery of electrical stimulation according to one or more programs that may specify stimulation parameters such as electrode combination, electrode polarity, stimulation current amplitude, pulse rate, and/or pulse width as well as the percentage of source current distributed among or contributed by a housing anode and one or more lead anodes on one or more leads, and the percentage of sink current sunk by one or more cathodes. Programs may be defined by a user via an external controller and transferred to an implantable stimulator 4 or 34 for use by stimulation control module 62.

Current regulator array 68 includes a plurality of regulated current sources or sinks Again, a current regulator may function as either a current source or sink, or be selectively configured to operate as either a source or a sink. For convenience, however, the term "current regulator" may be used in some instances to refer to either a source or sink. Hence, each of the current regulators in current regulator array 68 may operate as a regulated current source that delivers stimulation via a corresponding one of electrodes 48A-Q or a regulated current sink that receives current from a corresponding one of electrodes 48A-Q, where electrodes 48A-48Q may be provided on leads, on a stimulator housing, on a leadless stimulator, or in other arrangements. In general, electrodes 48A-48Q may be referred to below as electrodes 48 for conciseness.

Each switch of switch array 66 couples a corresponding one of electrodes 48 to either a corresponding bidirectional current regulator of current regulator array 68 or to reference voltage 64. In some examples, stimulation control module 62 selectively opens and closes switches in switch array 66 to configure a housing electrode, e.g., electrode 48Q, and one or more of electrodes 48A-48P on one or more leads as regulated electrodes by connection to regulated current sources or sinks in current regulator array 68. In other examples, stimulation control module 62 may selectively open and close switches in switch array 66 to configure either the housing electrode, e.g., electrode 48Q, or an electrode on the lead as an unregulated electrode by connection to reference voltage 64. In addition, stimulation control module 62 may selectively control individual regulated current sources or sinks in current regulator array 68 to deliver stimulation current pulses to the selected electrodes.

Reference voltage 64 may be a high or low voltage supplied by a regulated power source, depending on whether an electrode is programmed to be an unregulated source (high voltage rail) or unregulated sink (low voltage rail). Hence, reference voltage 64 may produce high and low reference voltages for selective coupling to unregulated, reference electrodes as needed given the selected electrode configuration. A regulated power source may produce one or more regulated voltage levels for use as reference voltage 64 and for use as a power rail for current regulator array 68. Again, although the same reference voltage 64 is coupled to current regulator array 68 in FIG. 5, different voltage levels could be used for the reference voltage coupled to switch array 66 and the operating voltage level provided to the regulated current source array. A regulated power source may generate the regulated voltages from voltages provided by a power source 54 (FIG. 3), such as a battery.

Stimulation control module 62 controls the operation of switch array 66 to produce electrode configurations defined by different stimulation programs. In some cases, the switches of switch array 66 may be metal-oxide-semiconductor field-effect-transistors (MOSFETs) or other circuit components used for switching electronic signals. The switches of switch array 66 may be designed to carry an amount of unregulated current that may be coupled to a corresponding electrode through an unregulated current path associated with reference voltage 64. As previously described, in some examples, two or more regulated stimulation electrodes 48 may be intentionally programmed to deliver different amounts of current such that the regulated electrodes produce an unbalanced current distribution.

To provide individual control of electrodes 48 as either regulated electrodes or as unregulated, reference electrodes, stimulation control module 62 controls operation of switch array 66, and current regulator array 68. When stimulation is delivered to patient 6, for the example of current pulses, stimulation control module 62 controls switch array 66 to couple selected stimulation electrodes for a desired electrode combination to respective current regulators of current regulator array 68 or to reference voltage 64, as needed. Stimulation control module 62 controls the regulated bidirectional current sources of current regulator array 68 coupled to regulated electrodes to source or sink specified amounts of current. For example, stimulation control module 62 may control selected current sources or sinks to on a pulse-by-pulse basis to deliver current pulses to corresponding electrodes.

Stimulation control module 62 also deactivates the regulated bidirectional current regulators of current regulator array 68 tied to inactive electrodes, i.e., electrodes that are not active as regulated electrodes in a given electrode configuration. Each regulated bidirectional current regulator of current regulator array 68 may include an internal enable switch controlled by stimulation control module 62 that disconnects regulated power source 64 from the current regulator or otherwise disables the current source when the corresponding electrode is not used as a regulated electrode to deliver stimulation.

In accordance with this disclosure, with reference to FIG. 3, at the time the stimulator 34 is implanted in the patient or set up to provide therapy via electrical stimulation to the patient, and the leads 48A-Q are placed, an image capturing device, such as the image capturing device 63 of programmer 40, may be utilized to capture an image of the lead placement in or on the patient. Captured images may be stored in memory 52 for retrieval by subsequent clinician or by the patient himself. Images stored in memory 52 of the stimulator 34 need not be retrieved by the same user who captured or stored them in memory 52. Additionally, stored images need not be retrieved by the same programmer 40 that captured and/or manipulated the images or at the same clinic or facility where the images were captured and/or manipulated. A subsequent programmer may retrieve images stored on memory 52 of an implantable stimulator 34 without requiring synchronization of the programmers.

Referring to FIG. 4, a user of programmer 40 may utilize user interface 59 to define an implant region where stimulation is to be applied by implantable stimulator 34. The implant region may be, for example, an anatomical region where electrodes are implanted, e.g., lumbar spine, epidural thoracic, etc. Additionally, the user may also define a target area of pain, which may be, for example, an anatomical region affected by the stimulation therapy, e.g., left leg, lower back, etc. All of or a sub-group of leads 48A-Q may be selected to deliver stimulations based on the defined implant region and/or target area of pain. In one example, the user of the programmer 40 may use the image capturing device 63 to capture an image of the placement of the implantable stimulator 34 and/or the placement of the leads delivering the therapy to the patient. The user may obtain an image by, for example, making a selection on the user interface 59 to capture a screen shot of the image as it appears on the user interface 59. The user may also capture the image using the image capturing device 63 by obtaining a digital photograph off of the screen or a print out of the screen of an imaging machine, e.g., a fluoroscopy machine, which may be connected to the programmer 40. The captured image may be an image, produced by a fluoroscopic imaging device, for example, and may be a still or a moving image. The captured image may also be an image produced by an imaging device or system such as, for example, an ultrasound, MRI, X-ray, CT, PET devices, or the like, and programmer 40 may obtain the image using via telemetry module 67, using digital media (e.g., removable hard drive), or by physically connecting the imaging system/device and programmer 40.

In accordance with this disclosure, the image capturing device 63 may be a camera built into the programmer 40 and may be controlled by the user interface 59 or may have its own control panel including, for example, a button to capture an image and various control media for focusing, zooming, rotating, panning, etc. Alternatively, the image capturing device 63 may be a camera connected to the programmer 40 via an interface, such as a universal serial bus (USB) interface. A copy of the captured image may be stored on memory 55 of programmer 40 and associated with a profile of the patient, which may be stored on memory 55. Programmer 40 may store multiple images with multiple, respective, patient profiles.

A captured image may be imported by a user, e.g., physician or clinician, into a therapy application, for further manipulation of the captured image. The user may define multiple implant regions in the captured image and placement of the leads within each region, to define the therapy delivered to the patient. Alternatively, a user may capture and import a separate image for each one of multiple implant regions and placement of the leads within each region, to define the therapy delivered in that implant region. The user may draw and position the leads on a graphical layer superimposed on top of the captured image(s), and may define the parameters of the electrical stimulation delivered (e.g., amplitude, pulse rate, pulse width, etc.) by selected electrodes on leads either as a group or separately.

The user may further manipulate the captured image using any of several image-manipulation functions such as, for example, positioning, zooming, panning, rotating, cropping, and placing annotations on the image. In one example, a programmer may automatically manipulate the captured image (e.g., positioning, zooming, panning, rotating, cropping, and the like) based on image processing techniques that identify the extent of the leads present in the captured image. In this example, the image processing techniques may identify the leads based on their contrast relative to the background, or by comparing the captured image with an image of the implant site without leads. In this example, the programmer may implement the manipulations automatically or may propose the manipulations to the user for confirmation. The user may also associate metadata with the captured image such as, for example, amount of zooming and panning applied to the image, a timestamp/date, therapy information, user/clinic information, storage location of the original full quality image (e.g., a hard drive at the clinic where the image was originally obtained), a URL to a location where the image may be stored on a network, coordinate offsets of key elements within the image (e.g. the coordinates of each electrode center), the scale of the image in dots per inch (DPI) or other units such that actual distances between elements can be later inferred, etc. Such information may be useful in image manipulation by a subsequent programmer that fetches the image stored in the stimulator 34 to determine past therapy delivered to the patient and based on that, future therapy. For example, a subsequent programmer may be able to utilize metadata associated with an image to work backwards and reconstruct an original view of the image using such information as, for example, amount of zoom, compression, cropping, interpolation, etc. Metadata may be also useful in reconstructing and restoring the image to utilize with the programmer 40, to ensure lead placements in future therapies is consistent with lead placements of previous therapies. When the user has completed manipulating the captured image and saved it to the memory 55 of the programmer 40, the user may transfer the image to the implantable stimulator 34. In some examples, the user may also associate the image with the patient, and add, delete, and save information associated with the image and/or the patient and the therapy the patient is receiving. In other examples, the user may manipulate images stored in the implanted medical device by adding more images, deleting existing images, or replacing existing images. The user may further manipulate images by printing images saved on the IMD, encrypting images, and transmitting images (e.g., via e-mail).

The implantable stimulator 34 may allocate a portion of the memory 52 for storing images transferred from the programmer 40. In one example, the user may apply compression techniques to reduce the size of captured images prior to transferring them to the implantable device 34. For example, the captured image may be converted to grayscale, cropped, converted to a format with more compression (e.g., JPEG), or the intensity and/or the contrast of the pixels may be reduced, among other techniques. Information regarding compression techniques utilized to reduce the size of the image may be also stored as metadata with an image, before transferring it to the stimulator 34. The user may employ iterative compression to reduce the size of the captured image, and ensure that the quality of the compressed image remains acceptable, such that a subsequent user is able to fully utilize the image. Iterative compression may involve compressing the captured image, determining whether more compression may be applied, and applying more compression if the image may be further compressed, or if no further compression is possible, utilizing other techniques to reduce the size of the image, such as cropping. The user may utilize the programmer in converting an image into a vector format, where pixel information may be discarded, and information regarding location and size of key elements (shapes of electrodes, outlines of vertebrae or other anatomical structures) may be encoded and stored in the device, allowing a programmer to later reconstruct a representative version of the image. The user may be able to view the resulting compressed images using different methods of compression and cropping to determine the image with the best quality using efficient compression. The user, e.g., a physician or clinician, may oversee the compression of the image to ensure that quality is retained while achieving a desired degree of compression for efficient storage on the IMD, which may have limited memory resources. After initial conversion to grayscale and conversion to a more efficient format, e.g., JPEG, the user may determine whether more compression is needed. If so, the image may be cropped and/or compressed further by, for example, reducing pixel intensity and/or contrast within the image, image scaling, or using other image encoding techniques. If the user determines that further compression is not possible, the user may determine to either crop the image and/or use different parameters in compressing the image.

In one example, programmer 40 may acquire the image and store it using a medical imaging standard such as, for example, the Digital Imaging and Communications in Medicine (DICOM) standard. In this example, programmer 40 may acquire and manipulate the image, and subsequently transfer it to an imaging system and/or device, thus allowing a user (e.g., clinician or physician) to view the image, and monitor or program the therapy provided to the patient.

In accordance with this disclosure, during a subsequent visit to a clinic or during a subsequent therapy session, the image stored on the stimulator 34 may be retrieved and displayed on an external device such as, for example, a subsequent programmer. The image stored on the stimulator may show the implant region and the leads implanted in that region such that, during a subsequent therapy session, a graphical layer of the leads may be placed on the image of the leads to improve therapy programming. The subsequent programmer need not be the same as programmer 40 that captured and manipulated the image, and need not be associated with the same clinic. In one example, a user may use programmer 40 to retrieve the image stored on stimulator 34, for transfer to another stimulator (e.g., when a stimulator is replaced). In another example, a user may user programmer 40 to retrieve the image stored on an external stimulator (e.g., used for trial during set up of therapy for a patient) and transfer the image to an implanted stimulator. In accordance with this disclosure, the image stored on the stimulator 34 may be retrieved, displayed, and utilized for further therapy independent of the programmer, user, or clinic providing therapy to the patient. A subsequent user may retrieve the images stored on the stimulator 34, and may place a layer of graphics on top of the image to apply therapy stimulations consistent with previous therapies. The layer of graphics may be, for example, a drawing of leads that may be manipulated to match the lead placement during a prior session or to match a planned therapy to be delivered to the area displayed in the imported image.

The images captured by the image capturing device 63 may be images of different regions to where therapies are delivered, where each image represents an anatomical implant region such as, for example, lumbar spine, epidural thoracic, etc., and the leads delivering the electrical stimulations in the region. The images may also represent different perspective of the same region, or images of the same region at different times, as lead placements and/or strength of the electrical stimulations provided by leads may vary in a time sequence within the same region during one therapy session. Obtaining and storing multiple perspectives of a lead placement may allow a programmer to subsequently infer information regarding the arrangement of the leads relative to anatomical structures in 3-dimensional space. Images may also represent therapies delivered to the same region over a number of previous sessions, which may allow a programmer to provide comparisons of the images over a time period to detect, for example, lead migration or other changes that may affect therapy. Furthermore, the images may be a video image or a sequence of still images displaying progress or change in lead placement and/or stimulations during a therapy session. A user may also transfer to the stimulator 34 a pointer indicating a location, on the web for example, where a copy of the captured image may be located, instead of transferring the image itself to the stimulator 34, when it may be desired to have access to the high resolution or original copy of the image before any compression or other manipulations were applied to the image.

Figure 6A:
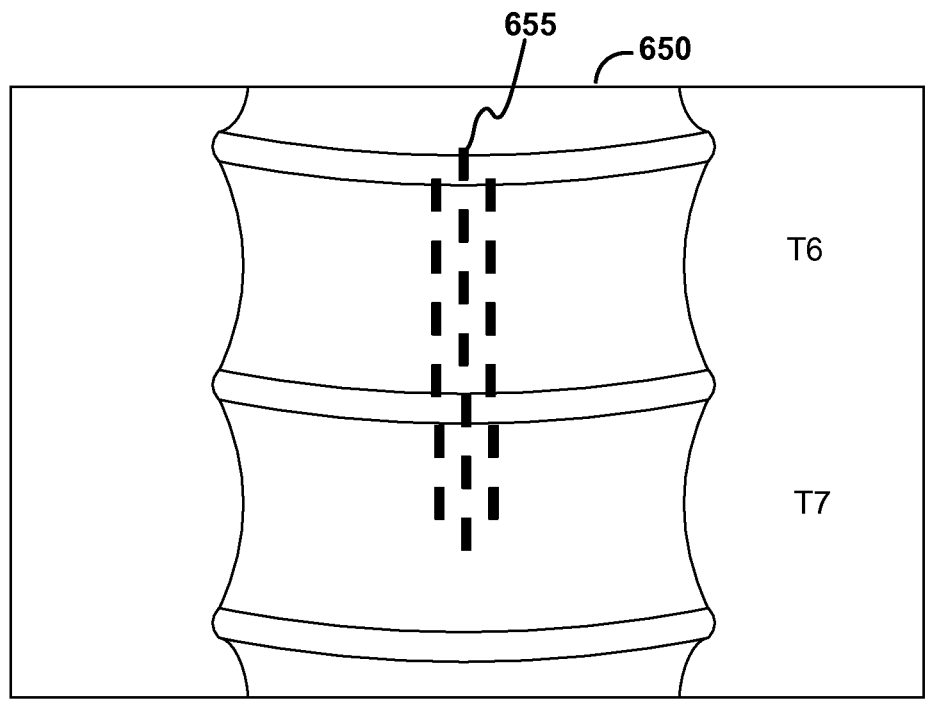
FIG. 6A illustrates an example image of an implant region captured by an image capturing device.

FIG. 6A illustrates an example image 650 of an implant region captured by an image capturing device. The image 650 may represent an implant region such as, for example, the lumbar spine or the epidural thoracic, where electrodes which provide stimulation therapy may be implanted. The image may be captured following implantation of the electrodes and may show the implanted electrodes 655.

Figure 6B:
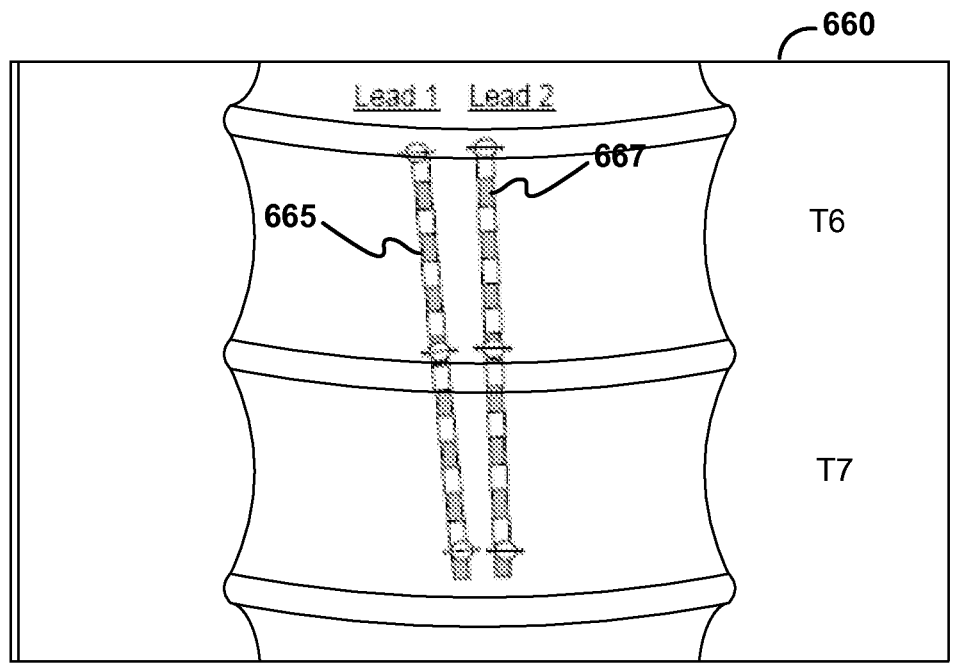
FIG. 6B illustrates an example image of an implant region being manipulated during programming.

FIG. 6B illustrates an example image 660 of an implant region being manipulated during programming. The image 660 may represent an implant region where electrodes may be implanted for delivery of therapy. The image may be captured and used in an initial therapy sessions or may be stored in an IMD and retrieved at a subsequent therapy session. During programming of a stimulation therapy, the image may be overlaid with a graphical representation 665 and 667 of the electrodes, in this example two. A user may manipulate the graphical representation of the electrodes to match the positioning of the implanted leads, which may be visible on the retrieved image.

Figure 7:
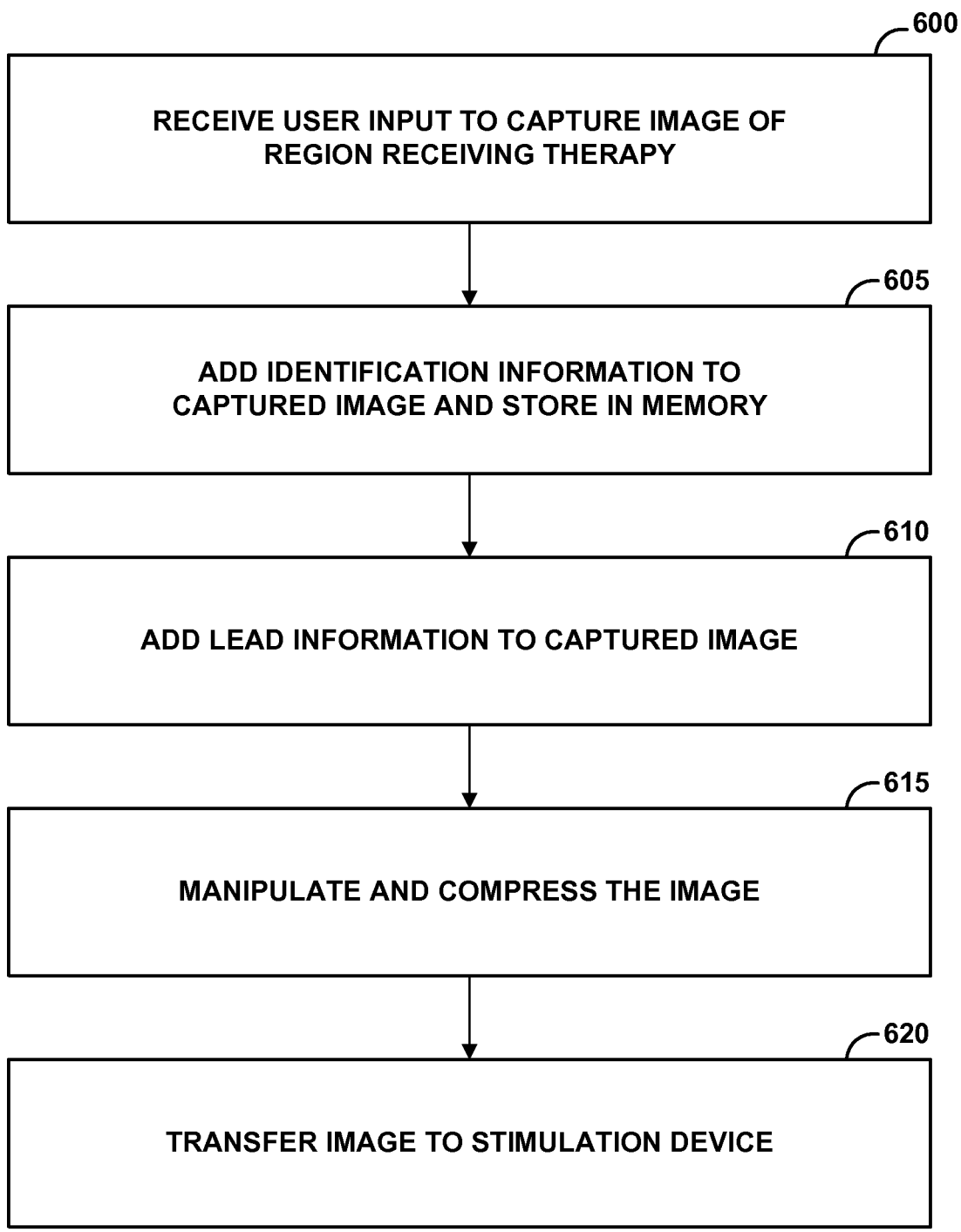
FIG. 7 is a flow diagram illustrating exemplary operation of a programmer in accordance with the techniques of this disclosure.

FIG. 7 is a flow diagram illustrating exemplary operation of a programmer in accordance with the techniques of this disclosure. In FIG. 6, a programmer, e.g., programmer 40 and in particular processor 53, may receive user input instructing it to capture an image using a connected image capturing device, e.g., image capturing device 63, of a region receiving therapy in a patient (600). The image capturing device 63 may be built into the programmer 40 or connected therewith via an interface. The region may be populated with leads, e.g., leads 48A-Q or a subgroup thereof, to provide stimulation therapy to the region. The image may be a screen shot of a display associated with the user interface 59 of the programmer 40, or a picture of a display or print out of a medical imaging device such as, for example, an fluoroscope machine, e.g., X-ray imaging device, an MRI device, a PET device, a CT device, and the like.

The programmer may add identification information to the captured image and store it on a storage unit associated with the programmer such as, for example, memory 55 (605). The identification information may be, for example, patient data, clinic information, physician, therapy applied, conditions, medications, etc. Alternatively, identification information may be grouped into a patient profile, which may be associated with a captured image and stored in memory 55.

The programmer then may be utilized by the user to add lead information to the captured image (610). The lead information may define placement and grouping of leads within the region shown in the captured image and/or amount of stimulation delivered by each lead or group of leads. The lead information may be used by a subsequent user during programming to select the appropriate graphical representation of the electrodes and/or to establish existing therapy parameters to better determine if and how to alter the stimulation therapy. Subsequently, the programmer may be used to manipulate and compress the image and prepare it to be transferred to the stimulation device (615). Manipulating the image may involve, for example, zooming, panning, or rotating the image and/or the leads to more accurately characterize the lead placement within the region captured in the image. Compressing the image may utilize a combination of compression techniques to achieve maximum compression while maintaining a certain quality of the image. Manipulating and compressing the image may be performed by a user or automatically by the programmer.

Once compression and manipulation of the image are completed, the programmer transfers the image, along with the associated image metadata, to the stimulation device (620). The transferred image may be stored in memory 52 of the stimulation device, e.g., stimulator 34, and may be set in an allocated portion of the memory for easier subsequent retrieval. These steps may be repeated for images of different lead implant regions, if a patient requires different therapies that require different lead placements, or images of the same region with different lead set ups, if the leads provide varying therapies over time. In another example, different images may be obtained of the same region at different points in time to determine whether leads move over time. In this example, a clinician may adjust the programmed therapy based on the new location of the leads, if he/she determines that the leads have moved. The programmer 40 may transfer the image using telemetry module 57 to communicate with the stimulator 34 via its telemetry module 56. The communication link between the stimulator and programmer may utilize an appropriate networking and communication standard.

In an example implementation using techniques of the disclosure, a user programmer 40 may be used to define one or more implant regions where leads may be implanted and used to provide stimulation therapy as defined by implantable stimulator 34. The stimulation may be applied using previously-defined lead placements and parameters or by defining lead placements and parameters. Multiple regions may be defined by the user, and for each region one or more leads may be used to deliver stimulation therapy.

The user may graphically define one or more desired lead implant regions using the user interface 59. The user interface may allow a user to view a combined image of the implant region where the leads may be implanted and graphical layer representing placement of the leads. The image of the region may be retrieved from the implantable stimulator 34 where it may have been stored during a previous session or may be captured by an image capturing device 63 during the current session. The retrieved image may show an image of the leads as they are implanted in the implant region, with annotations and metadata regarding the lead placement and stimulation therapy provided by the leads. The user may manipulate the graphical layer representation of the leads to match the image of the implanted leads.

An image capturing device 63 may be used to capture an image of the electrode placement for each of the therapy regions. The image capturing device 63 may be a camera built into the programmer 40 and may be controlled by the user interface 59 or may have its own control panel. Alternatively, the image capturing device 63 may be a camera connected to the programmer 40 via an interface, such as a universal serial bus (USB) interface.

A captured image may be manipulated by functions such as, for example, zooming, rotating, panning, cropping, and placing annotations on the image. The image may be compressed and other functions such as, cropping and converting to gray scale, for example, may be used to further reduce the size of the image. Metadata may be also associated with the image to enable a subsequent user to retrieve information regarding the region, the applied therapy, and other information related to the patient and the therapy received. The image may then be used to define therapy for a current session, or may be stored in the stimulator 34 for subsequent retrieval for future therapy.

The user may obtain an image by, for example, making a selection on the user interface 59 to capture a screen shot of the image as it appears on the user interface 59. The user may also capture the image using the image capturing device 63 by obtaining a digital photograph off of the screen or a print out of the screen of an imaging machine, e.g., a fluoroscopy machine, which may be connected to the programmer 40. The captured image may be an image, produced by a fluoroscopic imaging device, for example, and may be a still or a moving image. In another example, the image may be stored on a local or network drive, or a removable memory device.

The captured image may then be manipulated by the user for therapy application. The user may define multiple regions and the lead placement in the captured image. For each region, the user may define a set of leads to use for application of therapy to the region. The user may scale, stretch, move, or rotate the lead images to match the lead placement in the image of the therapy. Additionally, the user may perform other functions such as, for example, zooming, panning, and moving within the image, and adding annotations.

In one example, the therapy may be defined by specifying an electrode combination and specifying parameters associated with the leads and/or electrodes. In another example, the therapy may be defined using zone-based programming, through which the user may graphically define desired stimulation fields and may also define desired therapy intensity. Based on the defined stimulation field and therapy intensity, the contribution of each electrode used in the region may be automatically determined.

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

While aspects of this disclosure are described in the context of a programmer for an implanted medical device, techniques disclosed herein may be utilized in other fields and for other purposes. For example, images captured of specific regions during treatment of a patient may be acquired over a time period and utilized subsequently by other overseeing physicians to see progress of conditions or physiological changes. For example, the captured image may be of an MRI, CAT or PET scan, or any one of other diagnostic images associated with a patient and stored on an implanted device for subsequent physician visit. Aspects of this disclosure may be utilized to maintain patient privacy by storing information related to therapies received by the patient in devices associated only with the patient or implanted within the patient. Furthermore, aspects of this disclosure may reduce redundancy in treatments when a patient visits a clinic or physician different from the ones where he previously received treatment/therapy, by allowing any future clinic/physician to retrieve information stored in an implanted device to determine previous treatments received, regardless of where those treatments were received. Additionally, the techniques described in this disclosure may be utilized with other medical devices such as fluid and medical pumps, pacemakers, and the like.

Additionally, while aspects of this disclosure are described in the context of a stimulator as an IMD, techniques described herein may be utilized in other types of medical devices which may be implantable. For example, techniques of the disclosure may be utilized with any type of a neurostimulator, or implantable drug or insulin pumps where an image may show catheter configuration, and where therapy is delivered by pumping fluid such as blood, insulin, pain relief agents, or other medicine to the targeted therapy region.

For aspects implemented in software, at least some of the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to support one or more aspects of the functionality described in this disclosure.

Various examples of the invention have been described. These and other examples are within the scope of the following claims.

The invention claimed is:

1. A device for communication with an implantable medical device, the device comprising:
    an image acquisition device configured to obtain at least one image of at least one anatomical region of a patient and at least one medical lead implanted within the at least one anatomical region, wherein the at least one lead is associated with the implantable medical device; and
    a telemetry device configured to transmit the at least one image to the implantable medical device for storage in the implantable medical device.

2. The device of claim 1, wherein the device comprises a programmer for the implantable medical device, the programmer comprising a processor that generates one or more operational parameters for the implantable medical device.

3. The device of claim 1, wherein the at least one image comprises an image associated with a medical imaging device.

4. The device of claim 1, wherein the image acquisition device includes an image capture device configured to capture the image.

5. The device of claim 4, further comprising a housing, wherein the image capture device is integrated with the housing.

6. The device of claim 4, wherein the image capture device comprises a camera.

7. The device of claim 1, wherein the image acquisition device includes a processor that receives electronic image data representing the image.

8. The device of claim 7, wherein the processor is configured to receive the electronic image data via one of a removable data storage medium, a connection to an imaging device, or a network connection to an image storage device.

9. The device of claim 1, wherein the implantable medical device comprises a neurostimulator.

10. The device of claim 1, further comprising a user interface configured to receive user input that manipulates the at least one image.

11. The device of claim 10, wherein the user input indicates at least one of compressing, annotating, zooming within, panning, rotating, adding metadata to, associating with the patient, printing, transmitting, and encrypting the at least one image.

12. The device of claim 10, wherein the user input indicates adding to the at least one image information regarding at least one of the therapy delivered by the implantable medical device, the at least one anatomical region, and the patient.

13. The device of claim 1, wherein the telemetry device is configured to retrieve the at least one image from the implantable medical device.

14. A method comprising:
    obtaining by an image acquisition device at least one image of at least one anatomical region of a patient and at least one medical lead implanted within the at least one anatomical region, wherein the at least one lead is associated with an implantable medical device; and
    transmitting by a telemetry device the at least one image to the implantable medical device for storage in a storage device in the implantable medical device.

15. The method of claim 14, wherein a programmer for the implantable medical device comprises the image acquisition device and telemetry device, the method further comprising generating one or more operational parameters for the implantable medical device via a processor of the programmer.

16. The method of claim 14, wherein the at least one image comprises an image associated with a medical imaging device.

17. The method of claim 14, wherein obtaining by the image acquisition device the at least one image comprises capturing the image via an image capture device.

18. The method of claim 17, wherein the device comprises a housing, and wherein the image capture device is integrated with the housing.

19. The method of claim 17, wherein the image capture device comprises a camera.

20. The method of claim 14, wherein obtaining by the image acquisition device the at least one image comprises receiving electronic image data representing the image.

21. The method of claim 20, further comprising receiving the electronic image data via one of a removable data storage medium, a connection to an imaging device, or a network connection to an image storage device.

22. The method of claim 14, wherein the implantable medical device comprises a neurostimulator.

23. The method of claim 14, further comprising receiving user input via a user interface indicating manipulation of the at least one image.

24. The method of claim 23, further comprising at least one of compressing, annotating, zooming within, panning, rotating, adding metadata to, associating with the patient, printing, transmitting, and encrypting the at least one image in response to the user input.

25. The method of claim 23, further comprising adding to the at least one image information regarding at least one of the therapy delivered by the implantable medical device, the at least one anatomical region, and the patient in response to the user input.

26. The method of claim 14, further comprising retrieving the at least one image from the implantable medical device.

27. A device comprising:
means for obtaining at least one image of at least one anatomical region of a patient and at least one medical lead implanted within the at least one anatomical region, wherein the at least one lead is associated with an implantable medical device; and
means for transmitting the at least one image to the implantable medical device for storage in a storage device in the implantable medical device.

28. The device of claim 27, wherein the device comprises a programmer for the implantable medical device, further comprising means for generating one or more operational parameters for the implantable medical device.

29. The device of claim 27, wherein the at least one image comprises an image associated with a medical imaging device.

30. The device of claim 27, wherein the means for obtaining the at least one image comprises means for capturing the image via an image capture device.

31. The device of claim 30, further comprising a housing, wherein the image capture device is integrated with the housing.

32. The device of claim 27, wherein the image capture device comprises a camera.

33. The device of claim 27, wherein the means for obtaining the at least one image comprises means for receiving electronic image data representing the image.

34. The device of claim 33, further comprising means for receiving the electronic image data via one of a removable data storage medium, a connection to an imaging device, or a network connection to an image storage device.

35. The device of claim 27, wherein the implantable medical device comprises a neurostimulator.

36. The device of claim 27, further comprising means for receiving user input indicating manipulation of the at least one image.

37. The device of claim 36, further comprising means for at least one of compressing, annotating, zooming within, panning, rotating, adding metadata to, associating with the patient, printing, transmitting, and encrypting the at least one image in response to the user input.

38. The device of claim 36, further comprising means for adding to the at least one image information regarding at least one of the therapy delivered by the implantable medical device, the at least one anatomical region, and the patient in response to the user input.

39. The device of claim 27, further comprising means for retrieving the at least one image from the implantable medical device.

40. A non-transitory computer-readable medium comprising instructions that, upon execution, cause a processor to:
obtain by an image acquisition device at least one image of at least one anatomical region of a patient and at least one medical lead implanted within the at least one anatomical region, wherein the at least one lead is associated with the implantable medical device; and
transmit by telemetry device the at least one image to the implantable medical device for storage in a storage device in the implantable medical device.

41. The computer-readable medium of claim 40, wherein the instructions are executed by a processor in a programmer for the implantable medical device, further comprising instructions causing the processor in the programmer to generate one or more operational parameters for the implantable medical device.

42. The computer-readable medium of claim 40, wherein the at least one image comprises an image associated with a medical imaging device.

43. The computer-readable medium of claim 40, wherein the instructions to obtain the at least one image comprise instructions to capture the image via an image capture device.

44. The computer-readable medium of claim 43, wherein the computer-readable medium is housed in a housing, and wherein the image capture device is integrated with the housing.

45. The computer-readable medium of claim 43, wherein the image capture device comprises a camera.

46. The computer-readable medium of claim 40, wherein the instructions to obtain the at least one image comprise instruction to receive electronic image data representing the image.

47. The computer-readable medium of claim 46, further comprising instructions causing the processor to receive the electronic image data via one of a removable data storage medium, a connection to an imaging device, or a network connection to an image storage device.

48. The computer-readable medium of claim 40, wherein the implantable medical device comprises a neurostimulator.

49. The computer-readable medium of claim 40, further comprising instructions to receive user input that indicates manipulation of the at least one image.

50. The computer-readable medium of claim 49, further comprising instructions causing the processor to at least one of compress, annotate, zoom within, pan, rotate, add metadata to, associate with the patient, print, transmit, and encrypt the at least one image in response to the user input.

51. The computer-readable medium of claim 49, further comprising instructions causing the processor to add to the at least one image information regarding at least one of the therapy delivered by the implantable medical device, the at least one anatomical region, and the patient in response to the user input.

52. The computer-readable medium of claim 40, further comprising instructions causing the processor to retrieve the at least one image from the implantable medical device.

53. An implantable medical device comprising:
a therapy delivery module;
a processor that controls the therapy delivery module to deliver therapy;
a telemetry module that receives, from an external device via telemetry, at least one image of at least one anatomical region of a patient and at least one lead implanted within the at least one anatomical region, wherein the at least one lead is associated with the implantable medical device; and
a memory that stores the image.

54. The implantable medical device of claim 53, wherein the external device comprises a programmer.

55. The implantable medical device of claim 53, wherein the implantable medical device comprises a neurostimulator.

56. The implantable medical device of claim 53, wherein the telemetry module transmits the at least one image to an external device.

* * * * *